(12) United States Patent
Ueda et al.

(10) Patent No.: US 10,383,642 B2
(45) Date of Patent: Aug. 20, 2019

(54) SURGICAL PROCEDURE OF KNEE JOINT

(71) Applicant: OLYMPUS CORPORATION, Hachioji-shi, Tokyo (JP)

(72) Inventors: Sohei Ueda, Yamato (JP); Chie Onuma, Tama (JP); Manabu Ishikawa, Hachioji (JP); Michio Takayama, Tokyo (JP); Takamitsu Sakamoto, Hachioji (JP); Ken Fujisaki, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/337,271

(22) Filed: Oct. 28, 2016

(65) Prior Publication Data

US 2017/0119404 A1 May 4, 2017

Related U.S. Application Data

(63) Continuation-in-part of application No. 14/878,571, filed on Oct. 8, 2015.

(51) Int. Cl.
*A61B 17/16* (2006.01)
*A61B 17/32* (2006.01)
*A61B 17/17* (2006.01)
*A61B 17/56* (2006.01)

(52) U.S. Cl.
CPC ...... *A61B 17/1675* (2013.01); *A61B 17/1615* (2013.01); *A61B 17/32002* (2013.01); *A61B 17/320068* (2013.01); *A61B 17/1714* (2013.01); *A61B 2017/564* (2013.01)

(58) Field of Classification Search
CPC ........ A61B 17/1675; A61B 17/320068; A61B 17/1677
See application file for complete search history.

(56) References Cited

U.S. PATENT DOCUMENTS

| | | | |
|---|---|---|---|
| 5,067,962 A | * | 11/1991 | Campbell ................. A61F 2/08 128/898 |
| 6,544,260 B1 | | 4/2003 | Markel et al. |
| 8,709,089 B2 | | 4/2014 | Lang et al. |
| 2004/0068267 A1 | | 4/2004 | Harvie et al. |
| 2005/0054954 A1 | | 3/2005 | Lidgren et al. |

(Continued)

FOREIGN PATENT DOCUMENTS

| | | |
|---|---|---|
| JP | H05-168642 A | 7/1993 |
| JP | 2006-334268 A | 12/2006 |

OTHER PUBLICATIONS

U.S. Appl. No. 14/878,571, filed Oct. 8, 2015 in the name of Sohei Ueda, et al.

(Continued)

*Primary Examiner* — Olivia C Chang
(74) *Attorney, Agent, or Firm* — Oliff PLC

(57) ABSTRACT

A surgical procedure of preparing bone holes to fix an implanted tendon to a femur when performing reconstruction of a ligament in a knee joint, includes: bringing a treatment portion of an ultrasonic treatment instrument into contact with the femur in the knee joint, and applying ultrasonic vibration from the treatment portion to the femur, thereby cutting and forming a first bone hole from the inside of the knee joint to the femur in a predetermined depth.

14 Claims, 25 Drawing Sheets

(56) References Cited

U.S. PATENT DOCUMENTS

| | | | |
|---|---|---|---|
| 2006/0030871 A1 | 2/2006 | Hain et al. | |
| 2006/0253050 A1* | 11/2006 | Yoshimine | A61B 17/32006 601/2 |
| 2009/0018654 A1* | 1/2009 | Schmieding | A61B 17/1615 623/13.14 |
| 2010/0121197 A1 | 5/2010 | Ota et al. | |
| 2010/0174368 A1 | 7/2010 | Lynch et al. | |
| 2010/0191173 A1 | 7/2010 | Kimura et al. | |
| 2010/0298894 A1 | 11/2010 | Bojarski et al. | |
| 2010/0312350 A1 | 12/2010 | Bonutti | |
| 2011/0196401 A1 | 8/2011 | Robertson et al. | |
| 2012/0165843 A1 | 6/2012 | Gannoe et al. | |
| 2013/0006278 A1 | 1/2013 | Mayer et al. | |
| 2013/0096471 A1 | 4/2013 | Slayton et al. | |
| 2014/0230995 A1 | 8/2014 | Schlottig et al. | |
| 2015/0165243 A1 | 6/2015 | Slayton et al. | |
| 2016/0338782 A1* | 11/2016 | Bowling | A61B 90/39 |

OTHER PUBLICATIONS

U.S. Appl. No. 14/878,664, filed Oct. 8, 2015 in the name of Sohei Ueda, et al.
U.S. Appl. No. 14/878,684, filed Oct. 8, 2015 in the name of Sohei Ueda, et al.
Nov. 9, 2017 Office Action issued in U.S. Appl. No. 14/878,684.
Nov. 28, 2017 Office Action issued in U.S Appl. No. 14/878,664.
U.S. Appl. No. 15/337,596, filed Oct. 28, 2016 in the name of Michio Takayama et al.
Mar. 29, 2019 Office Action issued in U.S. Appl. No. 15/377,596.

* cited by examiner

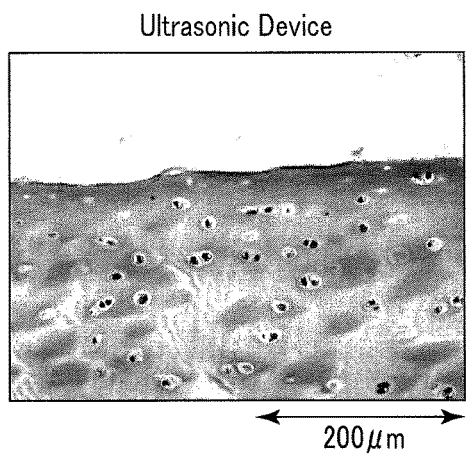
F I G. 9A
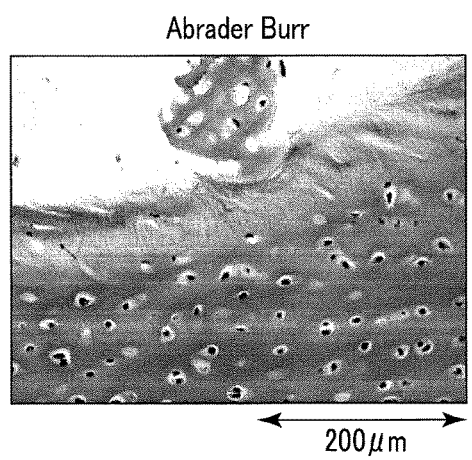
F I G. 9B
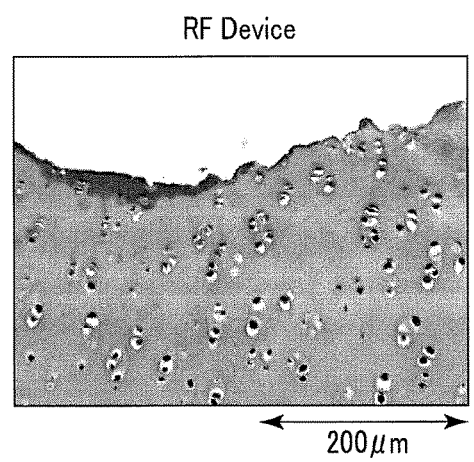
F I G. 9C

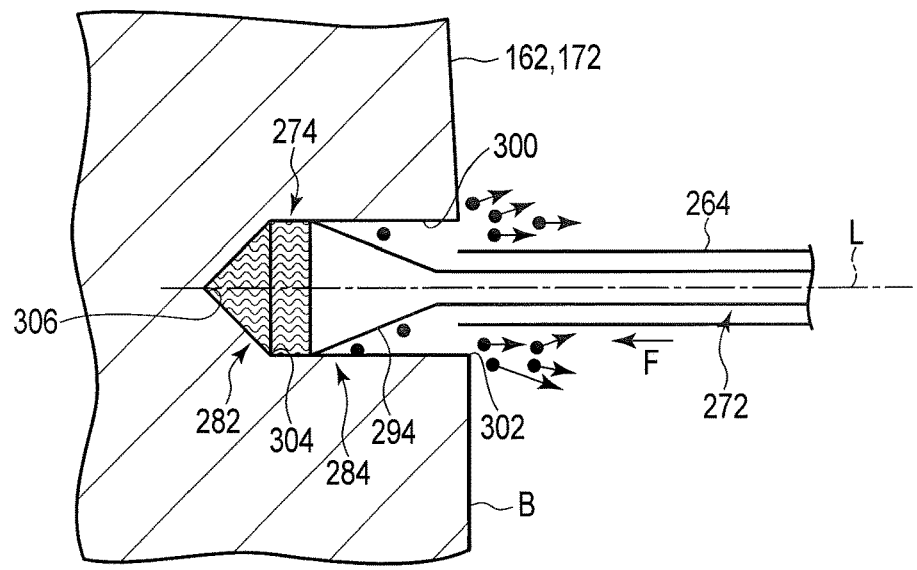
F I G. 18A
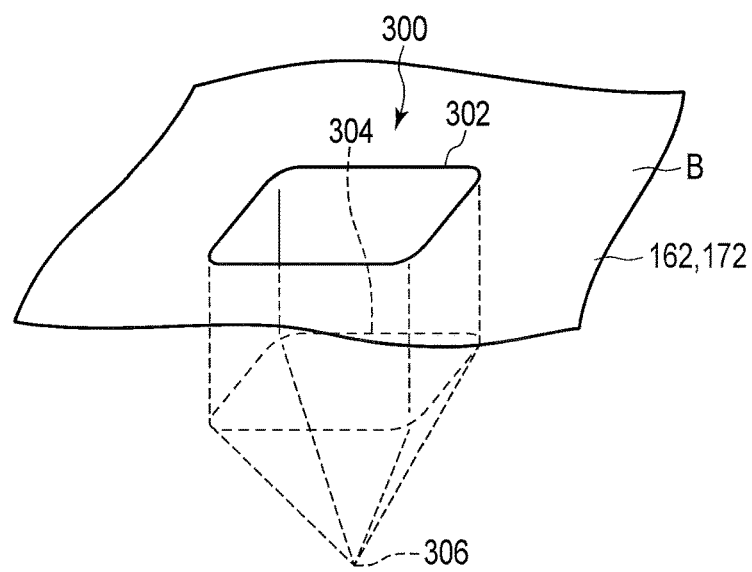
F I G. 18B

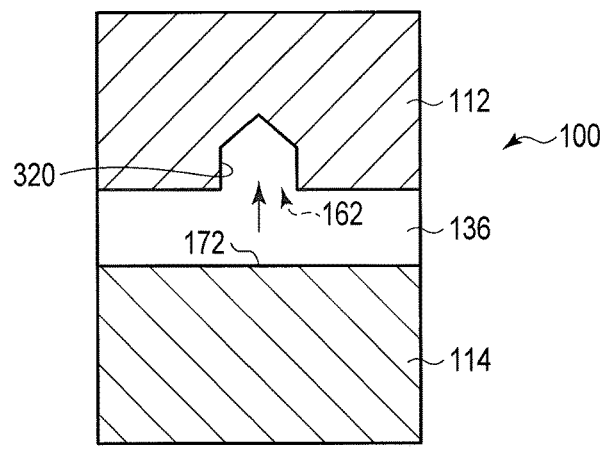
F I G. 22A
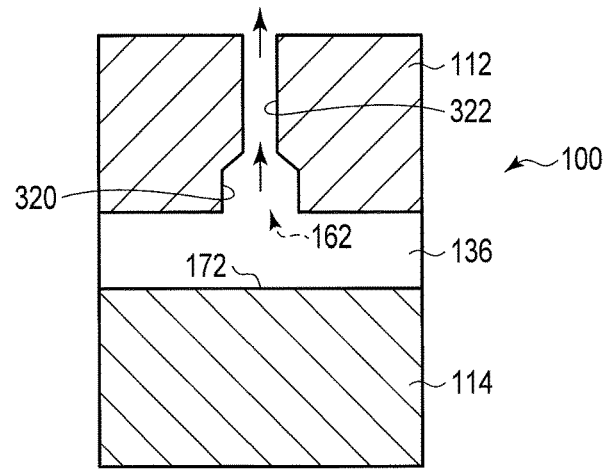
F I G. 22B
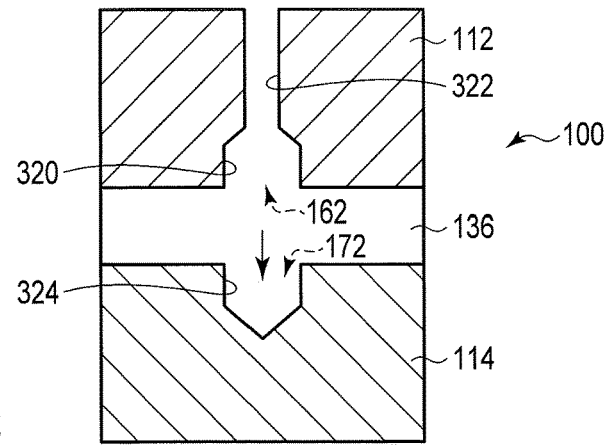
F I G. 22C

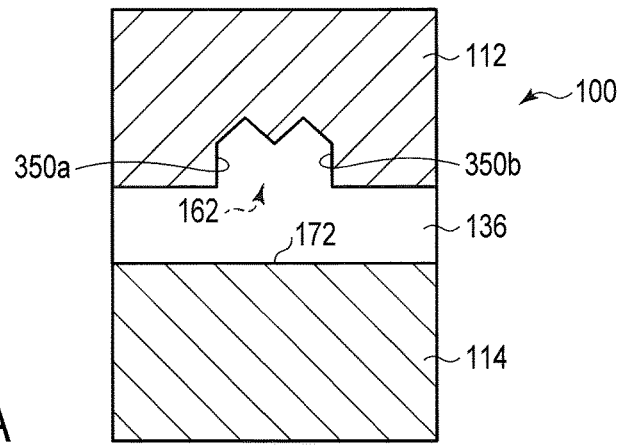
F I G. 25A
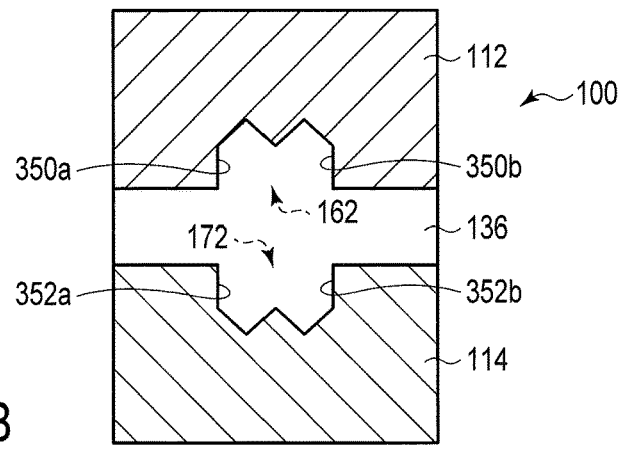
F I G. 25B
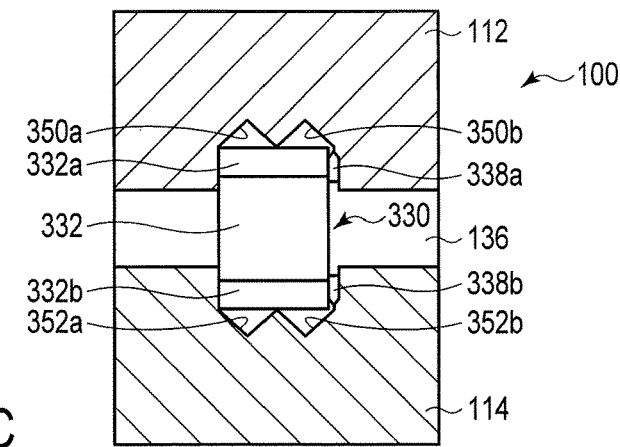
F I G. 25C

US 10,383,642 B2

SURGICAL PROCEDURE OF KNEE JOINT

CROSS REFERENCE TO RELATED APPLICATIONS

This application is a Continuation-in-Part Application of U.S. patent application Ser. No. 14/878,571, filed Oct. 8, 2015, the entire contents of all of which are incorporated herein by reference.

BACKGROUND OF THE INVENTION

1. Field of the Invention

This invention relates to a surgical procedure of a knee joint which is performed under an arthroscope.

2. Description of the Related Art

In a case where a surgeon performs reconstruction of a ligament in a knee joint, it is known that an outer shape of a cross section of an implant tendon, which is perpendicular to a longitudinal axis thereof, is a polygonal shape such as a rectangular shape, an elliptical shape, or an approximately polygonal shape close to the elliptical shape.

BRIEF SUMMARY OF THE INVENTION

According to one aspect of the present invention, a surgical procedure of preparing bone holes to fix an implanted tendon to a femur when performing reconstruction of a ligament in a knee joint, includes: bringing a treatment portion of an ultrasonic treatment instrument into contact with the femur in the knee joint, and applying ultrasonic vibration from the treatment portion to the femur, thereby cutting and forming a first bone hole from the inside of the knee joint to the femur in a predetermined depth.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 9A is a schematic view showing a state where a condition of a cartilage of a joint excised with the treating portion of the ultrasonic treatment device to which the ultrasonic vibration is transmitted is enlarged and observed;

FIG. 9B is a schematic view showing a state where a condition of the cartilage of the joint abraded with an abrader burr is enlarged and observed;

FIG. 9C is a schematic view showing a state where a condition of the cartilage of the joint excised with an RF device is enlarged and observed;

FIG. 18A is a schematic partial cross-sectional view showing a state where a hole is formed in a bone with the ultrasonic probe shown in FIG. 17A;

FIG. 18B is a schematic perspective view showing a concave hole formed in a predetermined orientation at a desired position of a footprint region of an anterior cruciate ligament with the ultrasonic probe shown in FIG. 18A;

FIG. 22A is a schematic view showing a procedure of the reconstruction of the anterior cruciate ligament and showing a state where a concave hole is formed from the inside of the knee joint to the footprint region of the anterior cruciate ligament of a femur of the knee joint with an ultrasonic treatment instrument;

FIG. 22B is a schematic view showing a state where a through-hole is formed to the concave hole of the femur in the state shown in FIG. 22A;

FIG. 22C is a schematic view showing a state where a concave hole is formed from the inside of the knee joint to a footprint region of an anterior cruciate ligament of a tibia of the knee joint in the state shown in FIG. 22B with the ultrasonic treatment instrument;

FIG. 25A is a schematic view showing a procedure of the reconstruction of the anterior cruciate ligament and showing a state where concave holes are formed from the inside of the knee joint to the footprint region of the anterior cruciate ligament of the femur of the knee joint with the ultrasonic treatment instrument to form a concave hole of a suitable size;

FIG. 25B is a schematic view showing a state where concave holes are formed from the inside of the knee joint to the footprint region of the anterior cruciate ligament of the tibia of the knee joint in the state shown in FIG. 25A with the ultrasonic treatment instrument to form a concave hole of a suitable size;

FIG. 25C is a schematic view showing a state where the implanted tendon including the BTB tendon shown in FIG. 23 is fixed to the femur and the tibia with screws.

DETAILED DESCRIPTION OF THE INVENTION

Embodiments of this invention will be described with reference to the drawings.

Figure 1:
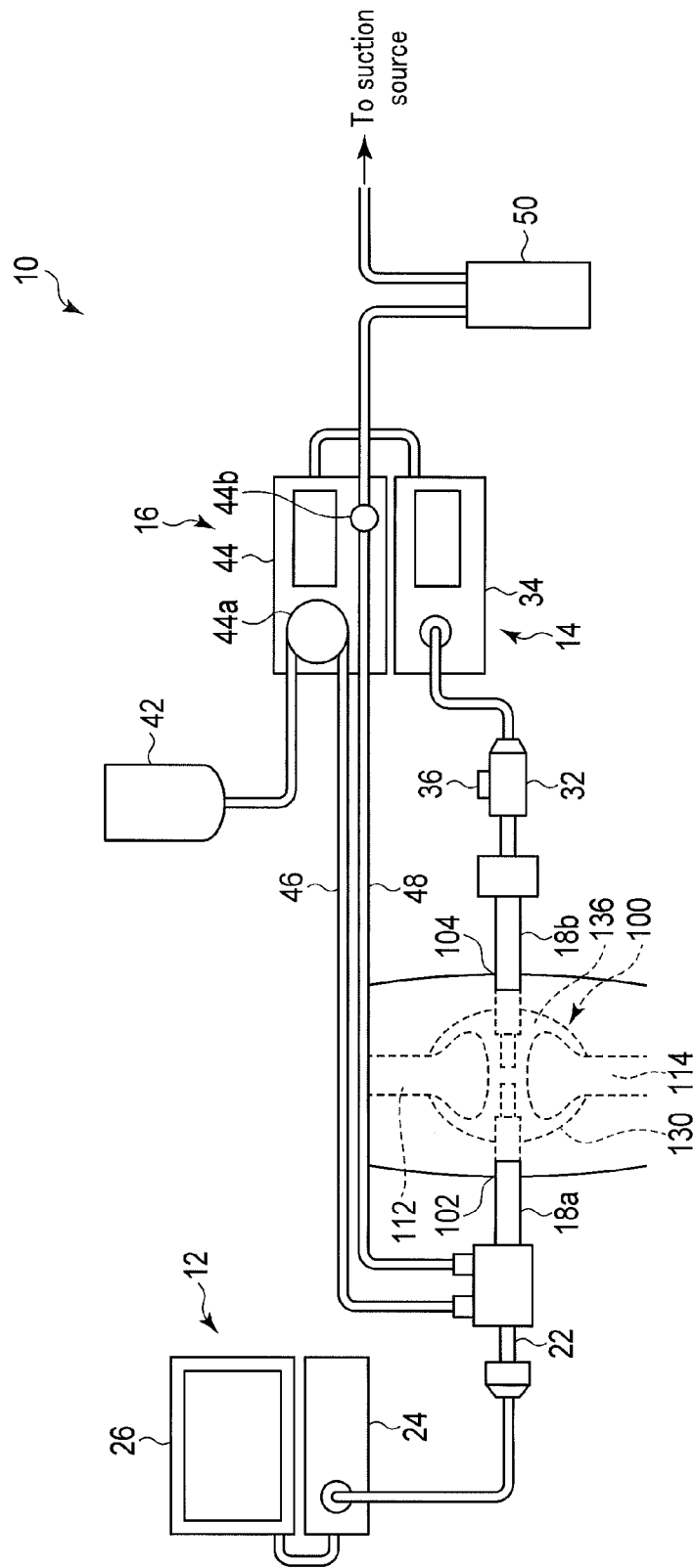
FIG. 1 is a schematic view showing a treatment system for use in a surgical treatment of a knee joint.

When a knee joint 100 is treated, for example, a treatment system 10 shown in FIG. 1 is used. The treatment system 10 has an arthroscope device 12, a treatment device 14, and a perfusion device 16.

The arthroscope device 12 includes an arthroscope 22 to observe an inner part of the knee joint 100, i.e., the inside of a joint cavity 136 of a patient, an arthroscope controller 24 that performs image processing on the basis of a subject image imaged by the arthroscope 22, and a monitor 26 that displays the image generated by the image processing in the arthroscope controller 24. The arthroscope 22 is inserted into the joint cavity 136 of the knee joint 100 through a first cannula 18a that forms a lateral portal 102 via which the inner part of the knee joint 100 of the patient communicates with an outer side of skin. It is to be noted that a position of the portal 102 is not uniform but is suitably determined in accordance with a patient's condition.

The treatment device 14 has an ultrasonic treatment device 32, a treatment device controller 34, and a switch 36. Here, the treatment device controller 34 supplies energy to the ultrasonic treatment device 32 in accordance with an operation of the switch 36 to transmit an ultrasonic vibration to a treating portion 68 of an after-mentioned probe 66 of the ultrasonic treatment device 32. The treatment device 32 is inserted into the joint cavity 136 of the knee joint 100 through a second cannula 18b that forms a medial portal 104 via which the inner part of the joint 100 of the patient communicates with the outer side of the skin. It is to be noted that a position of the portal 104 is not uniform but is suitably determined in accordance with the patient's condition. The switch 36 maintains, for example, a driven state of an ultrasonic transducer in a state where the switch is pressed to be operated, and when the pressed state is released, the driven state of the ultrasonic transducer is released.

Here, it is described that the one switch 36 is disposed, but the switches may be disposed. An amplitude of the ultrasonic transducer can suitably be set by the treatment device controller 34. In consequence, by the operation of the switch 36, a frequency of the ultrasonic vibration to be output from the after-mentioned ultrasonic transducer is the same, but the amplitude may be different. Therefore, the switch 36 can suitably switch the amplitude of the ultrasonic transducer to states such as two large and small states. For example, when the amplitude can be switched to the two large and small states, the ultrasonic vibration of the small amplitude is for use in treating comparatively soft tissues such as a synovial membrane 134, cartilages 112a, 114a and 118a, and meniscuses 142 and 144 shown in FIG. 3 to FIG. 5. The ultrasonic vibration of the large amplitude is for use in treating comparatively hard tissues such as bones (a femur 112, a tibia 114 and a patella 118) shown in FIG. 3 and FIG. 4.

It is to be noted that, for example, the two switches 36 may be disposed in parallel, or a hand switch and a foot switch may selectively be used. Additionally, when the one switch 36 is switched to be used, the ultrasonic vibration of the small amplitude may be output by one operation, and the ultrasonic vibration of the large amplitude may be output by two quick pressing operations as in a double click operation of a mouse for a computer.

The perfusion device 16 includes a bag-shaped liquid source 42 that contains a perfusion liquid such as physiological saline, a perfusion pump unit 44, a liquid supply tube 46 whose one end is connected to the liquid source 42, a liquid discharge tube 48, and a suction bottle 50 connected to one end of the liquid discharge tube 48. The suction bottle 50 is connected to a suction source attached to a wall of an operating room. In the perfusion pump unit 44, the perfusion liquid can be supplied from the liquid source 42 by a liquid supply pump 44a. Additionally, in the perfusion pump unit 44, suction/suction stop of the perfusion liquid in the joint cavity 136 of the knee joint 100 to the suction bottle 50 can be switched by opening/closing a pinching valve 44b as a liquid discharge valve.

The other end of the liquid supply tube 46 that is a liquid supply tube path is connected to the first cannula 18a. In consequence, the perfusion liquid can be supplied into the joint cavity 136 of the knee joint 100 via the first cannula 18a. The other end of the liquid discharge tube 48 that is a liquid discharge tube path is connected to the first cannula 18a. In consequence, the perfusion liquid can be discharged from the joint cavity 136 of the knee joint 100 via the first cannula 18a. It is to be noted that, needless to say, the other end of the liquid discharge tube 48 may be connected to the second cannula 18b, so that the perfusion liquid can be discharged from the knee joint 100.

It is to be noted that, here, the perfusion liquid can be supplied and discharged through the first cannula 18a, but a function that is capable of supplying and/or discharging the perfusion liquid may be imparted to, for example, the arthroscope 22. Similarly, the function that is capable of supplying and/or discharging the perfusion liquid may be imparted to the ultrasonic treatment device 32. In addition, a function that is capable of supplying and discharging the perfusion liquid through the second cannula 18b may be imparted. Furthermore, the perfusion liquid may be supplied and discharged through separate portals.

Figure 2:
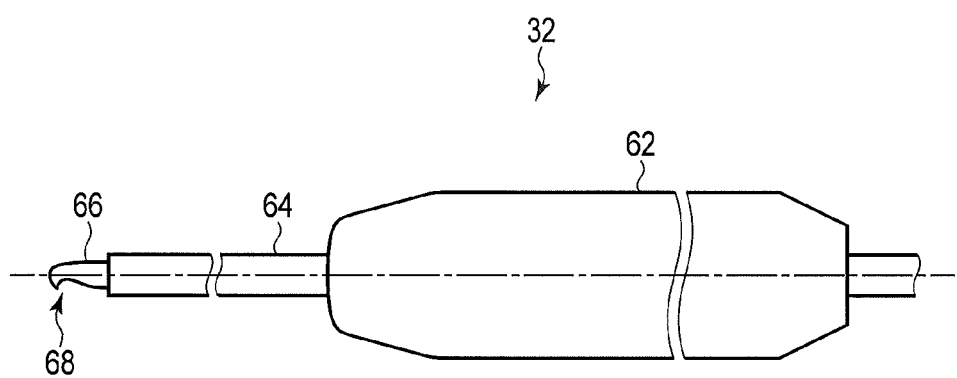
FIG. 2 is a schematic view showing one example of an ultrasonic treatment device (an ultrasonic device) of the treatment system for use in the surgical treatment of the knee joint.

As shown in FIG. 2, the ultrasonic treatment device 32 includes a housing 62, a sheath 64 projected from the housing 62, and the probe 66 inserted into the sheath 64. In particular, outer peripheral surfaces of the housing 62 and the sheath 64 have insulating properties. The probe 66 is made of a metal material such as a titan alloy material capable of transmitting the ultrasonic vibration. To a proximal end of the probe 66, there is fixed an unshown ultrasonic transducer unit disposed in the housing 62. In the ultrasonic treatment device 32, the treating portion 68 of the probe 66 inserted into the sheath 64 is disposed together with the sheath 64 in the joint cavity 136 through the second cannula 18b. Further, when the switch 36 is pressed, energy is supplied from the treatment device controller 34 to the ultrasonic transducer unit fixed to the proximal end of the probe 66, and the ultrasonic transducer ultrasonically vibrates. This vibration is transmitted from the proximal end of the probe 66 toward a distal end side, and hence with the aid of the treating portion 68 of a distal end of the probe 66, the hard tissue (the bone tissue or the like) can be resected and the soft tissue (the cartilage, a membrane tissue or the like) can be excised.

It is to be noted that a shape of the treating portion 68 can suitably be selected in accordance with a treatment region. Here, there is described an example where a hook type of treating portion shown in FIG. 2 is used, but various shapes such as a rake type, a blade type and a curette type can selectively be used in consideration of an accessibility to the treatment region, an adaptability to the treatment on the basis of a position, a shape, a size or the like of a blade portion of the treating portion 68, or the like.

A structure of the knee joint 100 will briefly be described. Hereinafter, the knee joint 100 of a right knee will be described as an example.

Figure 3:
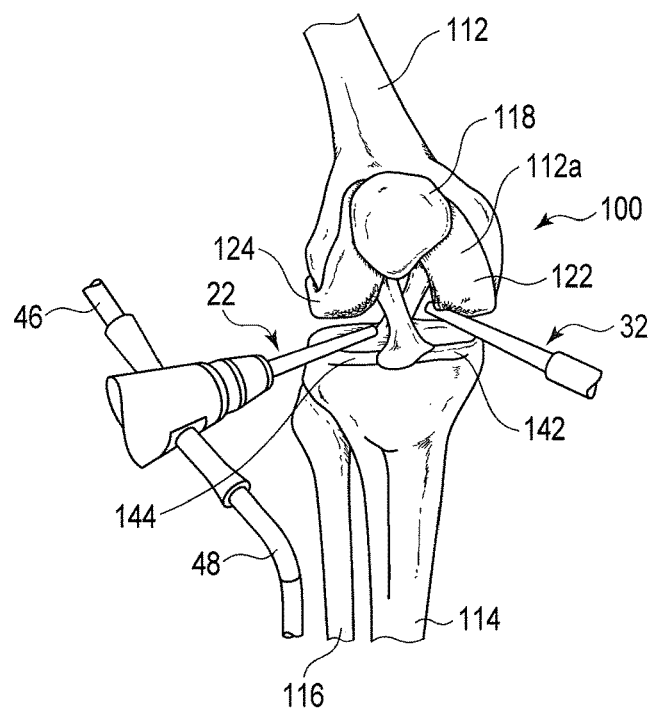
FIG. 3 is a schematic view showing a state where an arthroscope and a treating portion of the ultrasonic treatment device are inserted from separate portals, respectively, to an articular capsule of the knee joint of a right knee seen from the anterior side.
Figure 4:
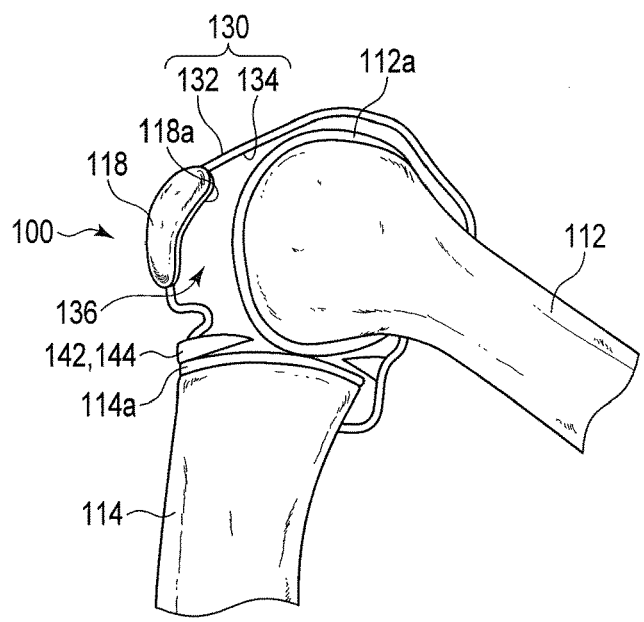
FIG. 4 is a schematic side view showing a state where the knee joint of the right knee encapsulated in the articular capsule is seen from the medial side.

As shown in FIG. 3, the knee joint 100 is mainly constituted of a femur 112, a tibia 114, a fibula 116, and a patella 118. As shown in FIG. 4, the knee joint 100 is encapsulated in a joint capsule 130. The joint capsule 130 includes a fibrous tunica 132 on a lateral side and the synovial membrane 134 on a medial side. The synovial membrane 134 forms pleats and secretes a synovial fluid, and hence the knee joint 100 smoothly moves. The inside of the joint capsule 130 is called the joint cavity 136. The joint cavity 136 is filled with the synovial fluid to be secreted from the synovial membrane 134. The joint cavity 136 of the knee joint 100 is incompletely divided into four cavities (a suprapatellar bursa, a patellofemoral joint cavity, a lateral femorotibial joint cavity and a medial femorotibial joint cavity), and the synovial membrane pleat is present as a partition wall between these cavities.

Additionally, in the knee joint 100, each of the cartilages (joint cartilages) 112*a*, 114*a* and 118*a* is present between the bones (the femur 112, the tibia 114 and the patella 118). By the cartilages 112*a*, 114*a* and 118*a*, impact can be absorbed in the knee joint 100, and the knee joint 100 can smoothly move.

As shown in FIG. 3, surfaces of the femur 112 which are joined to the tibia 114 are referred to as a medial condyle 122 and a lateral condyle 124, respectively. In a superior surface of the tibia 114, there are two surfaces to be joined to the medial condyle 122 and the lateral condyle 124 of the femur 112. Between the medial condyle 122 and the lateral condyle 124 of the femur 112 and the superior surface of the tibia 114, the meniscuses 142 and 144 and ligaments 152 and 154 adhere.

Figure 5:
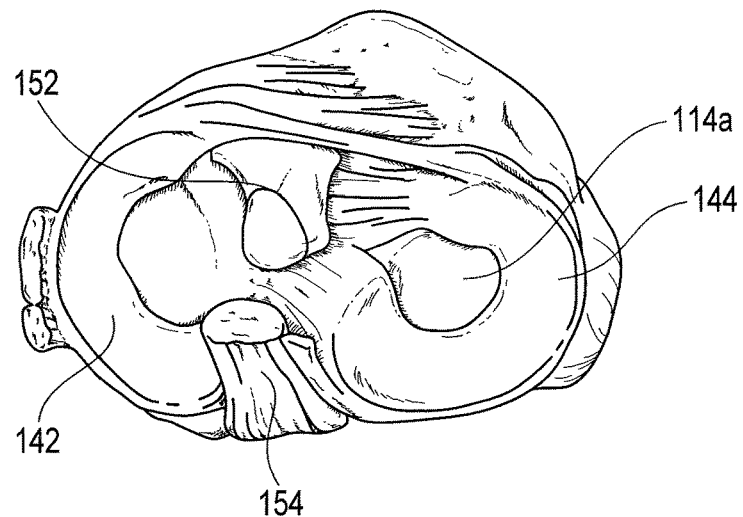
FIG. 5 is a schematic view showing a state where a medial meniscus, a lateral meniscus, an anterior cruciate ligament and a posterior cruciate ligament of the knee joint of the right knee are seen from the superior side.

As shown in FIG. 5, the meniscuses 142 and 144 form a pair on lateral and medial sides. A superior surface of the medial meniscus 142 extends along the spherical cartilage 112*a* disposed in the medial condyle 122 of the femur 112, and an inferior surface of the medial meniscus extends along the flat cartilage 114*a* disposed on the superior surface of the tibia 114. Similarly, a superior surface of the lateral meniscus 144 extends along the spherical cartilage 112*a* disposed in the lateral condyle 124 of the femur 112, and an inferior surface of the lateral meniscus extends along the flat cartilage 114*a* disposed on the superior surface of the tibia 114. Consequently, the meniscuses 142 and 144 are formed so that lateral edge portions of the meniscuses are thick and medial edge portions of the meniscuses are thin. It is to be noted that the lateral edge portions of the medial meniscus 142 and the lateral meniscus 144 are linked to the joint capsule 130.

In the knee joint 100, an anterior cruciate ligament 152 and a posterior cruciate ligament 154 are present. When the knee joint 100 is seen from an anterior side, the anterior cruciate ligament 152 is present in the anterior side and the posterior cruciate ligament 154 is present in a posterior side. One end of the anterior cruciate ligament 152 is passed through a space between the medial condyle 122 and the lateral condyle 124 of the femur 112 and fixed to the posterior side of the femur, and the other end of the anterior cruciate ligament is fixed to the anterior side of the superior surface of the tibia 114. The anterior cruciate ligament 152 has its start region in a medial surface posterior region of the lateral condyle 124 of the femur 112, and adheres to an anterior intercondylar fossa area (an end region) of the tibia 114. One end of the posterior cruciate ligament 154 is fixed to a slightly anterior region of the femur 112, and the other end of the posterior cruciate ligament is fixed to the posterior side of the superior surface of the tibia 114. The posterior cruciate ligament 154 has its start region in a lateral surface anterior region of the medial condyle 122 of the femur 112, and adheres to a posterior intercondylar fossa area (an end region) of the tibia 114.

Next, there will be described a method in which a surgeon (an operator) uses the treatment system 10 mentioned above to excise a damaged region of the meniscus 142 or 144 under the arthroscope 22 to the patient who has the damaged region in at least one of the meniscuses 142 and 144 present between the femur 112 and the tibia 114 of the knee joint 100.

Figure 6:
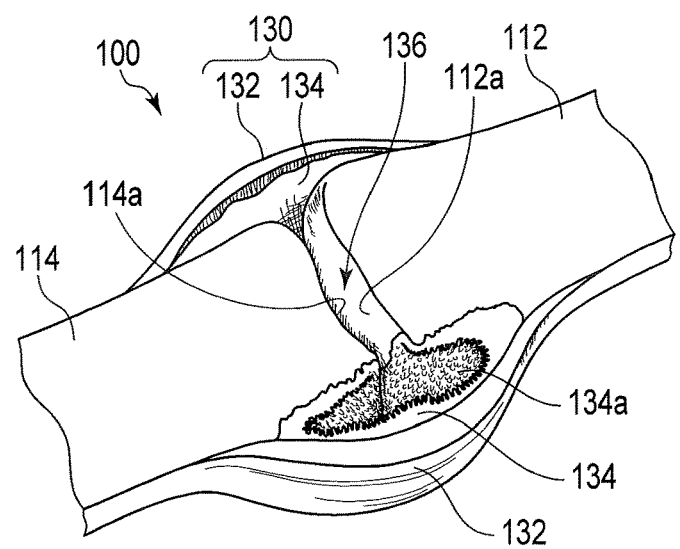
FIG. 6 is a schematic coronary cross-sectional view schematically showing a state where there is inflammation of a synovial membrane in the articular capsule of the knee joint.

As to the damage of the meniscus 142 or 144 of the knee joint 100, in general, there are a case where the meniscus is damaged due to an external injury or the like and a case where the meniscus is damaged due to repeatedly loaded stress. As to the meniscus 142 or 144, the damages are mainly and often caused to an anterior horn of the medial meniscus 142 or posterior regions (posterior horns or posterior nodes) of the medial meniscus 142 and the lateral meniscus 144. In addition, when the meniscus 142 or 144 is damaged, as shown in FIG. 6, such inflammation as shown by a reference sign 134*a* might be caused to the meniscus together with the synovial membrane 134.

A condition of the knee joint 100 is confirmed by use of an X-ray, MRI or the like. When the damage is confirmed in the meniscus 142 or 144, a damaged condition of the meniscus 142 or 144 is confirmed in advance.

There are prepared an instrument to form the portals 102 and 104 in the knee joint 100, and an instrument for use in a surgical treatment of excising an inflamed region of the synovial membrane 134 and damaged regions of the meniscuses 142 and 144. It is to be noted that the treating portion 68 of the ultrasonic treatment device 32 is formed into a suitable shape such as the hook type.

The surgeon forms the first portal 102 on anterior and lateral side of the knee joint to the patient who bends the knee joint 100 of the right knee. When necessary, the first cannula 18*a* is disposed in the portal 102. A distal end of the arthroscope 22 is disposed in the joint cavity 136 of the knee joint 100 through the first cannula 18*a*. Here, the first cannula 18*a* is not necessarily required, when the perfusion device 16 is connectable to the arthroscope 22.

The joint cavity 136 of the knee joint 100 is filled with saline by use of the perfusion device 16. In this state, the medial side of the joint cavity 136 of the knee joint 100 is suitably observed by using the arthroscope 22. Further, the damaged region of the meniscus 142 or 144 is disposed in a view field of the arthroscope 22 to confirm the damage. In addition, an inflamed condition of the synovial membrane 134 on the medial side of the joint capsule 130 of the knee joint 100 is confirmed.

The surgeon forms the second portal 104 on the anterior and medial side to the patient who bends the knee joint 100.

Figure 7:
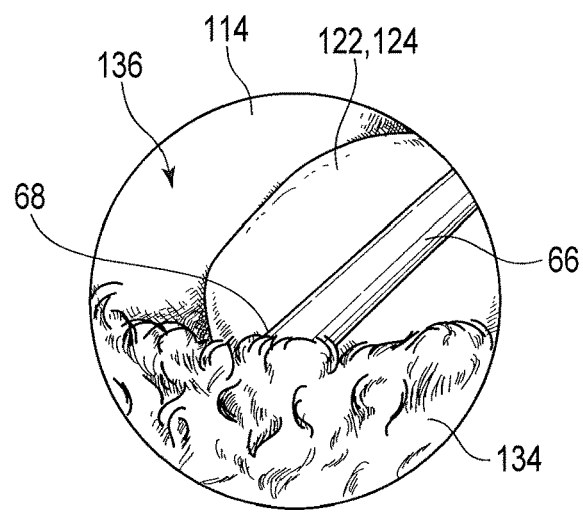
FIG. 7 is a schematic view showing a state where an ultrasonic vibration is transmitted to the treating portion of the ultrasonic treatment device to excise the synovial membrane in the articular capsule of the knee joint under the arthroscope.

When necessary, the second cannula 18b is disposed in the portal 104. The treating portion 68 of the ultrasonic treatment device 32 is disposed in the joint cavity 136 of the knee joint 100 through the second cannula 18b. When the inflamed region is present in the synovial membrane 134 of the joint capsule 130 confirmed with the arthroscope 22, as shown in FIG. 7, the surgeon approaches the inflamed region with the treating portion 68 of the ultrasonic treatment device 32 to bring the treating portion into contact with the inflamed region while observing the inflamed region with the arthroscope 22. Further, the surgeon operates the switch 36 of the treatment device 14 to generate the ultrasonic vibration of the suitable amplitude in the ultrasonic transducer, thereby only moving the treating portion 68 in an axial direction of the probe 66, whereby the inflamed region 134a of the synovial membrane 134 and/or an inflamed synovial membrane is excised with the treating portion 68 to which the vibration is transmitted. The excised inflamed region of the synovial membrane 134 is flown with momentum in excising the region. At this time, the surgeon suitably moves the ultrasonic treatment device 32 and also suitably moves the arthroscope 22 to excise the inflamed region 134a of the synovial membrane 134 and/or the inflamed synovial membrane and further a peripheral region with the treating portion 68 of the ultrasonic treatment device 32 while always disposing the treating portion 68 in the view field of the arthroscope 22. In the synovial membrane 134, the excised inflamed region 134a and the peripheral region are discharged to the suction bottle 50 through the first cannula 18a and the liquid discharge tube 48.

A head (a treating portion) of an unshown shaver that has heretofore been used in removing the inflamed region of the synovial membrane 134 or the like has a structure to intertwine the inflamed region by periaxial rotation. Thus, the shaver performs the treatment while intertwining (winding) the inflamed region, and hence there is a high possibility that a peripheral tissue in the knee joint 100 is wound during the treatment. In addition, power is securely transmitted from a motor of the shaver to the head, and hence it is difficult to form a portion between the motor and the head of the shaver into a suitable shape, and additionally, a head portion is formed to be larger than the treating portion 68 of the ultrasonic treatment device 32. In consequence, it is very difficult for the head portion of the shaver to especially access the posterior side of the knee joint 100. Therefore, even by use of the shaver that has heretofore been used, it might be difficult to remove the synovial membrane 134. When the treatment is performed by using the ultrasonic treatment device 32, it is not necessary to rotate the treating portion 68. Therefore, damages due to the winding of the peripheral tissue in the knee joint 100 can be decreased. In addition, when the treatment is performed by using the ultrasonic treatment device 32, the treating portion 68 can be formed into the suitable shape, the treating portion 68 can be formed to be smaller, and the probe 66 can be formed to be thinner, so that a moving range of the treating portion 68 to the second cannula 18b can be increased. Therefore, in a case where the ultrasonic treatment device 32 is used, for example, the posterior side of the knee joint 100 can more easily be accessed as compared with a case where the shaver is used. Consequently, in the case the ultrasonic treatment device 32 is used, the inflamed region of the synovial membrane 134 can more easily be excised than in the case where the shaver is used.

In addition, as described above, the shaver has the structure to intertwine the inflamed regions of the synovial membrane 134 by the periaxial rotation. Consequently, the shaver operates to tear off the synovial membrane 134, and the excised region of the synovial membrane 134 easily bleeds. On the other hand, the treating portion 68 of the ultrasonic treatment device 32 does not periaxially rotate, and the inflamed region can be excised only by moving the treating portion in the axial direction of the probe 66. Further, in the case where the ultrasonic treatment device 32 is used, the excised region is flown unlike the case where the shaver is used, and hence the view field of the arthroscope 22, especially the view field of the treatment region is easily acquired.

Figure 8:
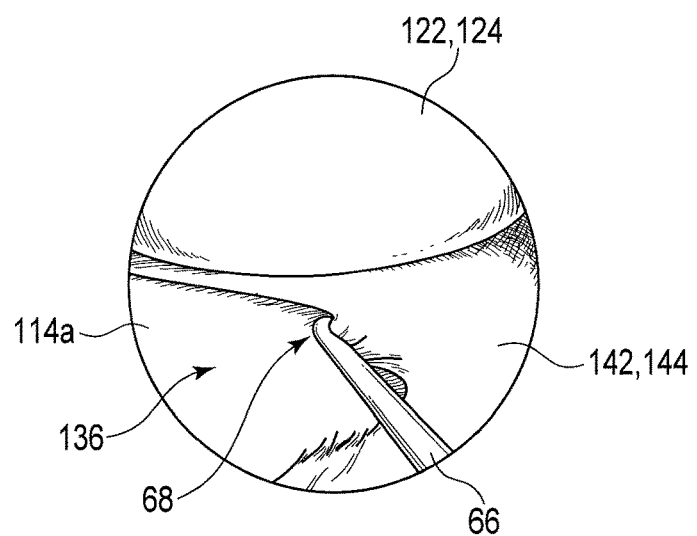
FIG. 8 is a schematic view showing a state where the ultrasonic vibration is transmitted to the treating portion of the ultrasonic treatment device to excise a damaged region of the meniscus of the knee joint under the arthroscope.

As described above, the surgeon removes the inflamed region of the synovial membrane 134 by use of the ultrasonic treatment device 32, and then while moving the arthroscope 22 to confirm the inside of the joint cavity 136 of the knee joint 100, the surgeon moves the ultrasonic treatment device 32 to dispose the damaged region of the meniscus 142 or 144 in the view field of the arthroscope 22 as shown in FIG. 8. Furthermore, the treating portion 68 of the ultrasonic treatment device 32 is disposed to face the damaged region of the meniscus 142 or 144. That is, here, the treating portion 68 of the ultrasonic treatment device 32 that is the same as the portion used to excise the synovial membrane 134 is disposed as it is to face the damaged region of the meniscus 142 or 144. Therefore, the treating portion 68 approaches treatment regions such as the anterior horn of the medial meniscus 142 and the posterior horns and posterior nodes of the medial meniscus 142 and the lateral meniscus 144 to face them. The treating portion 68 of the ultrasonic treatment device 32 is brought into contact with the treatment region of the meniscus 142 or 144, and the switch 36 is operated to generate the ultrasonic vibration of the suitable amplitude in the ultrasonic transducer. In consequence, the treating portion 68 to which the ultrasonic vibration is transmitted is only moved in the axial direction of the probe 66, to remove the damaged meniscus 142 or 144 in the treatment region. That is, a region of the meniscus 142 or 144 in which tear or damage denaturation occurs is excised with the treating portion 68 to which the ultrasonic vibration is transmitted, to perform dissection. As shown in FIG. 10B, the surgeon can easily form a surface treated by the treating portion 68 of the ultrasonic treatment device 32 to which the ultrasonic vibration is transmitted, as a smooth surface without forming any corner portions in the treatment region of the meniscus 142 or 144 by suitably moving the treating portion 68 in accordance with the movement of the probe 66 in the axial direction. When the treatment object region of the meniscus 142 or 144 is removed, a dented region having a substantially circular vertical cross section is formed, and there are smoothly continued a removed surface 146 from which the treatment object region of the meniscus 142 or 144 is removed and a non-removed surface adjacent to the removed surface 146. In consequence, the region treated with the treating portion 68 of the ultrasonic treatment device 32 by the surgeon is hard to be stuck on another region.

It is to be noted that, by the operation of the switch 36, the amplitude of the ultrasonic transducer in a case where the synovial membrane 134 is removed may be adjusted to be different from the amplitude of the ultrasonic transducer in a case where the damaged region of the meniscus 142 or 144 is excised.

It might be difficult for the unshown shaver head that has heretofore been used in shaving the bone to access the damaged region of the meniscus 142 or 144. The ultrasonic treatment device 32 can be formed into a suitable shape between the proximal end of the probe 66 and the treating portion 68 of the distal end, the treating portion 68 can be formed to be small, and hence the ultrasonic treatment device can more easily have access toward the posterior side of the knee joint 100 than the shaver. Consequently, in the case where the treatment is performed by using the ultrasonic treatment device 32, the damaged region of the meniscus 142 or 144 can more easily be excised than in the case where the shaver is used. Additionally, as shown in FIG. 9A, the surface treated by the ultrasonic treatment device 32 can smoothly be formed by, for example, a blade surface of the hook-shaped treating portion 68. On the other hand, the shaver shaves the surface by the rotation of the head, and hence it is more difficult to smoothen the cut-off surface than in the case where the ultrasonic treatment device 32 is used.

It is to be noted that when an abrader burr is used in the treatment of a soft tissue such as the meniscus 142 or 144, the treated surface (an abraded surface) is disadvantageously made fluffy as shown in FIG. 9B. Consequently, in the case where the abrader burr is used, it is more difficult to smoothen the surface and it is easier to generate concave and convex areas in the excised region than in the case where the ultrasonic treatment device 32 is used. As shown in FIG. 9A and FIG. 9B, in the case where the treating portion 68 of the ultrasonic treatment device 32 is used, the treated surface is more easily formed precisely and smoothly than in the case where the abrader burr is used. Therefore, in the case where the ultrasonic treatment device 32 is used, the concave and convex areas of the excised region can be decreased as compared with the case where the abrader burr is used.

Thus, the ultrasonic treatment device 32 is used, and hence the device can smoothly be moved between the treatment region of the meniscus 142 or 144 and the femur 112 and between the treatment region of the meniscus 142 or 144 and the tibia 114. Therefore, the treatment in which the ultrasonic treatment device 32 is used contributes to a smooth joint movement in which sticking of the femur 112 to the meniscus 142 or 144 that remains to be excised and sticking of the tibia 114 to the meniscus 142 or 144 that remains to be excised are eliminated.

As described above, the surgeon performs the treatment of the damaged region of the meniscus 142 or 144 to the patient. Afterward, the surgeon pulls out the treating portion 68 of the ultrasonic treatment device 32 from the second cannula 18b and pulls out the distal end of the arthroscope 22 from the first cannula 18a. Furthermore, the first and second cannulas 18a and 18b are removed from the knee joint 100. Further, the portals 102 and 104 are sutured.

As described above, the technique of excising the damaged region of the meniscus 142 or 144 under the arthroscope 22 can be considered as follows.

By use of the treatment system 10, the surgeon can perform a series of treatment of excising the synovial membrane 134 and excising the damaged region of the meniscus 142 or 144 with the treating portion 68 of the ultrasonic treatment device 32 while the one ultrasonic treatment device 32 is disposed as it is in the second cannula 18b. Consequently, during the surgical treatment, the surgeon does not need to replace the treatment device 32 disposed in the joint cavity 136, and hence surgical treatment time can be shortened.

The probe 66 of the ultrasonic treatment device 32 can be formed into the suitable shape, and the treating portion 68 can be formed to be smaller than the shaver or the abrader burr. Consequently, in the treatment in which the ultrasonic treatment device 32 is used, a movable range to the second cannula 18b can be increased, and treatment regions such as the anterior horn of the medial meniscus 142 and the posterior horns and posterior nodes of the medial meniscus 142 and the lateral meniscus 144 can more easily be approached as compared with the case where the shaver is used. Additionally, in the treatment of the ultrasonic treatment device 32, the more precise and smoother treated surface can be formed than in the case where the shaver or the abrader burr is used. Consequently, for example, when the surgeon performs the treatment by use of the ultrasonic treatment device 32 and then the patient bends and stretches the knee joint 100 to move the meniscus 142 or 144, the meniscus can be prevented from being stuck on the femur 112 or the tibia 114, which can contribute to the smooth joint movement.

In addition, the surgeon uses the ultrasonic treatment device 32 and hence does not have to use a high frequency device (an RF device). As shown in FIG. 9C, when the treatment is performed by using the high frequency device, there is the fear that the surface (an inferior bone of the cartilage) is invaded by heat. On the other hand, as shown in FIG. 9A, in the case where the ultrasonic treatment device 32 is used, for example, the cartilage 114a of the tibia 114 under the meniscus 142 or 144 is less invaded by heat, and thermal necrosis is prevented from being caused to the cartilage 114a in the treated surface excised by the treating portion 68, as compared with the case where the high frequency device is used.

Next, there will be described a method in which the surgeon uses the treatment system 10 mentioned above to perform a surgical treatment of excising a damaged region of the cartilage 112a under the arthroscope 22 to the patient who has the damaged region in the spherical cartilage 112a. Here, together with the removal of the synovial membrane 134 and the treatment of the damaged region of the meniscus 142 or 144, there is described a method of removing a denatured cartilage in a case where osteochondritis dissecans (OCD) occur.

The knee joint 100 might cause the osteochondritis dissecans. The surgeon confirms the osteochondritis dissecans by use of MRI or the like. Degrees of progress of the osteochondritis dissecans are indicated as, for example, grades of ICRS (International Cartilage Repair Society), i.e., Grade 0 (Normal), Grade 1 (Stable, continuity: Softened area covered by intact cartilage), Grade 2 (Partial discontinuity, stable on probing), Grade 3 (Complete discontinuity, "dead in situ", not dislocated), Grade 4 (Dislocated fragment, loose within the bed or empty defect. >10 mm in depth is B-subgroup). In the knee joint 100, the cartilages 112a are damaged in, for example, the medial condyle 122 and the lateral condyle 124 of the femur 112 due to the osteochondritis dissecans.

There are prepared the instrument to form the portals 102 and 104 in the knee joint 100, and an instrument for use in a surgical treatment of excising the cartilage and the bone. It is to be noted that the treating portion 68 of the ultrasonic treatment device 32 is formed into the suitable shape, e.g., the hook type.

The surgeon disposes the distal end of the arthroscope 22 in the joint cavity 136 of the knee joint 100 of the patient through the first cannula 18a. The surgeon fills the joint cavity 136 of the knee joint 100 of the patient with the saline (the perfusion liquid) by use of the perfusion device 16. In this state, the surgeon suitably observes the inside of the joint cavity 136 of the knee joint 100 of the right knee by use of the arthroscope 22. Further, the surgeon disposes the damaged region of the meniscus 142 or 144 in the view field of the arthroscope 22 to confirm the damage. Additionally, the surgeon confirms the inflammation of the synovial membrane 134 in the joint capsule 130 of the knee joint 100.

The surgeon disposes the treating portion 68 of the ultrasonic treatment device 32 in the joint cavity 136 of the knee joint 100 of the patient through the second cannula 18*b*. In a case where a region that causes inflammation is present in the synovial membrane 134 of the joint capsule 130 confirmed with the arthroscope 22, the surgeon excises the inflamed region from the synovial membrane 134 with the treating portion 68 of the ultrasonic treatment device 32 to which the ultrasonic vibration is transmitted, while observing the inflamed region with the arthroscope 22. Similarly, the ultrasonic vibration is transmitted to the same treating portion 68 of the ultrasonic treatment device 32 to excise the damaged region of the meniscus 142 or 144. That is, when necessary, the inflamed region of the synovial membrane 134 or the damaged region of the meniscus 142 or 144 is excised as described above, or when possible, the damaged region of the meniscus 142 or 144 is sutured and treated.

For example, when the cartilage 112*a* attached to the medial condyle 122 of the femur 112 is damaged, the surgeon confirms the grade of the osteochondritis dissecans with the arthroscope 22. By use of the arthroscope 22, the surgeon confirms whether a part of the cartilage 112*a* is softened (Grade 1), whether laceration such as partial tear is present in a part of the cartilage 112*a* (Grade 2), whether a part of the cartilage 112*a* is discontinued from a bone (the medial condyle 122 of the femur 112) to which the cartilage 112*a* adheres (Grade 3), or whether a bone cartilage piece is liberated and the bone (the medial condyle 122 of the femur 112) to be hidden behind the cartilage 112*a* is exposed (Grade 4), to judge the grade. Additionally, in each of Grades 1 to 4, presence/absence of the bone spurs and presence/absence of hardened regions are confirmed to the medial condyle 122 and the lateral condyle 124 of the femur 112.

Figure 10A:
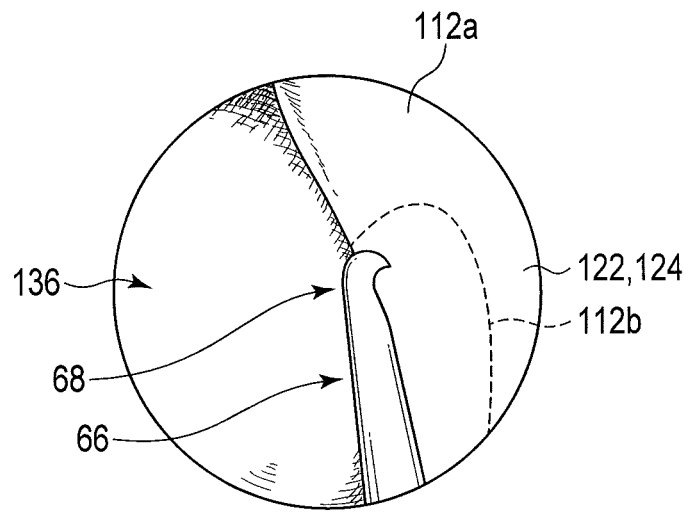
FIG. 10A is a schematic view showing a state where the ultrasonic vibration is transmitted to the treating portion of the ultrasonic treatment device to remove a treatment object region of the cartilage of the knee joint under the arthroscope.
Figure 10B:
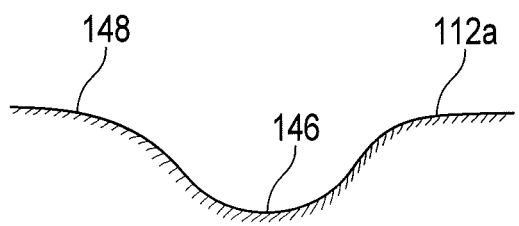
FIG. 10B is a schematic view showing a condition where of a treated surface formed by the treating portion of the ultrasonic treatment device when the ultrasonic vibration is transmitted to the treating portion of the ultrasonic treatment device to remove the treatment object region of the cartilage of the knee joint under the arthroscope.

Further, as shown in FIG. 10A, the treating portion 68 of the ultrasonic treatment device 32 is brought into contact with the treatment object region of the cartilage 112*a* while observing the treatment object region always disposed in the view field of the arthroscope 22. In this state, the switch 36 is operated to suitably perform the treatment to the treatment object region by use of the ultrasonic vibration. At this time, as shown in FIG. 10B, the surgeon can easily form the treated surface by the treating portion 68 to which the ultrasonic vibration of the ultrasonic treatment device 32 is transmitted, as the smooth surface without forming any corner portions therein, by suitably moving the treating portion 68 in accordance with the movement of the probe 66 in the axial direction. As shown in FIG. 10B, when the treatment object region of the cartilage 112*a* is removed, a dented region having a substantially circular vertical cross section is formed, and there are smoothly continued the removed surface from which the treatment object region of the cartilage 112*a* is removed and the non-removed surface adjacent to the removed surface. In consequence, the region treated with the treating portion 68 of the ultrasonic treatment device 32 by the surgeon is hard to be stuck on another region.

Here, as shown in FIG. 10B, the treatment is performed without leaving any corner portions in treated regions of the cartilage 112*a* when the surgeon judges as one of Grade 2 to Grade 4, as well as the softened region 112*b* of the cartilage 112*a* is removed.

When the surgeon judges that a condition of a part of the cartilage 112*a* is Grade 2, as shown in FIG. 10A, the treating portion 68 of the ultrasonic treatment device 32 is faced to a torn region (a treatment object region) 112*b* of the cartilage 112*a*. Further, the torn region of the cartilage 112*a* is removed by moving the treating portion 68 along the axial direction of the probe 66 while transmitting the ultrasonic vibration to the treating portion 68 of the ultrasonic treatment device 32. In addition, the bone spur formed in Grade 2 is removed by transmitting the ultrasonic vibration to the treating portion 68 of the ultrasonic treatment device 32. Also at this time, the treatment is performed without leaving any corner portions in treated regions of the cartilage 112*a* and the medial condyle 122 of the femur 112.

When the surgeon judges that the condition of a part of the cartilage 112*a* is Grade 3, as shown in FIG. 10A, the treating portion 68 of the ultrasonic treatment device 32 is faced to the torn region (the treatment object region) 112*b* of the cartilage 112*a* and a torn region of the medial condyle 122 of the femur 112. Further, the torn region 112*b* of the cartilage 112*a* and the torn region of the medial condyle 122 of the femur 112 are removed together with the osteophyte formed in the medial condyle 122 of the femur 112 and the like, by moving the treating portion 68 along the axial direction of the probe 66 while transmitting the ultrasonic vibration to the treating portion 68 of the ultrasonic treatment device 32. Also at this time, the treatment is performed without leaving any corner portions in the treated regions of the cartilage 112*a* and the medial condyle 122 of the femur 112.

When the surgeon judges that the condition of a part of the cartilage 112*a* is Grade 4, the torn region (the treatment object region) 112*b* of the cartilage 112*a* shown in FIG. 10A might peel from the medial condyle 122 of the femur 112. In this case, when the inferior bone (the medial condyle 122 of the femur 112) of the cartilage 112*a* undergoes necrosis due to an interruption in circulation of blood or the like, the bone cartilage piece separates to be liberated as a loose body in the joint capsule 130. In addition, the loose body might be separated also from the cartilage 112*a* into the joint capsule 130. In such a case, the treating portion 68 of the ultrasonic treatment device 32 is faced to the torn region 112*b* of the cartilage 112*a* and the torn region of the medial condyle 122 of the femur 112. Further, the torn region 112*b* of the cartilage 112*a* and the torn region of the medial condyle 122 of the femur 112 are removed together with the bone spur formed in the medial condyle 122 of the femur 112, by moving the treating portion 68 along the axial direction of the probe 66 while transmitting the ultrasonic vibration to the treating portion 68 of the ultrasonic treatment device 32. Also at this time, the treatment is performed without leaving any corner portions in the treated regions of the cartilage 112*a* and the medial condyle 122 of the femur 112. It is to be noted that the region liberated from the cartilage 112*a* is sucked or curetted to be removed. Further, excision of the deformed cartilage 112*a*, removal of the curetted or liberated cartilage piece, and grafting of the cartilage 112*a* are carried out. For example, when the bone cartilage piece is grafted, a region to be grafted needs to be dissected. In this case, the ultrasonic vibration is transmitted to the treating portion 68 of the ultrasonic treatment device 32 to smoothly continue the removed surface and the non-removed surface adjacent to the removed surface as shown in FIG. 10B, thereby carrying out the dissection. Further, the bone cartilage piece is fixed by a known method.

Thus, in accordance with the condition, the treating portion 68 is moved along the axial direction of the probe 66 while transmitting the ultrasonic vibration to the treating portion 68 of the ultrasonic treatment device 32, to suitably dissect the cartilage 112*a*. In addition, the ultrasonic vibration is transmitted to the treating portion 68 of the same ultrasonic treatment device 32, to remove the bone spur. Also when the bone spur is removed, the treatment is performed without leaving any corner portions and the smooth surface is formed without forming any corner portions in the same manner as shown in FIG. 10B.

Here, there has been described the example where the cartilage 112a of the femur 112 and the femur 112 are treated, but the inferior cartilage 118a (see FIG. 4) of the patella 118 in chondromalacia patellae can similarly be treated.

As described above, the technique of removing the damaged region 112b of the cartilage 112a under the arthroscope 22 can be considered as follows.

By use of the treatment system 10, the surgeon can perform a series of treatment of removing the cartilage 112a and the treatment object region of the femur 112 with the treating portion 68 of the treatment device 32 while the one ultrasonic treatment device 32 is disposed as it is in the second cannula 18b. Consequently, by use of the treatment system 10, the surgeon can perform a series of treatment of excising the synovial membrane 134, excising the damaged region of the meniscus 142 or 144 and removing the cartilage 112a and the treatment object region of the femur 112 with the treating portion 68 of the treatment device 32 while the one ultrasonic treatment device 32 is disposed as it is in the second cannula 18b.

Further, the surgeon has heretofore replaced and used different instruments to the portal 104 by, for example, using the shaver or the like in a smoothening treatment of the cartilage 112a and using the abrader burr or the like in the smoothening treatment of the femur 112, the tibia 114 or the patella 118. When the cartilage 112a and the treatment object region 112b of the femur 112 are removed, the ultrasonic treatment device 32 does not have to be replaced to the portal 104. These treatments can be performed with the one ultrasonic treatment device 32. Consequently, during the surgical treatment, the surgeon does not have to replace the treatment device 32 disposed in the joint cavity 136, and hence the surgical treatment time can be shortened.

The probe 66 of the ultrasonic treatment device 32 can be formed into the suitable shape, and the treating portion 68 can be formed to be smaller than the shaver or the abrader burr. Consequently, in the treatment in which the ultrasonic treatment device 32 is used, the movable range to the cannula 18b can be increased, and treatment regions such as back surfaces or the like of the medial condyle 122 and the lateral condyle 124 of the femur 112 and a treatment region of a joint surface (an inferior surface) of the patella 118 can more easily be approached as compared with the case where the shaver or the abrader burr is used. Additionally, in the treatment of the ultrasonic treatment device 32, the more precise and smoother treated surface can be formed than in the case where the shaver or the abrader burr is used. Consequently, for example, when the surgeon performs the treatment by use of the ultrasonic treatment device 32 and then the patient bends and stretches the knee joint 100 to move the femur 112, the tibia 114 and the patella 118, the femur 112, the tibia 114 and the patella 118 can be prevented from being stuck on one another, which can contribute to the smooth joint movement.

The abrader burr abrades the bone (the bone spur) that is the hard tissue by the periaxial rotation, and hence loads that act on the abrader burr increase in a case where the bone is abraded. Consequently, the abrader burr might noticeably entirely be vibrated by the loads onto the treating portion. On the other hand, the treating portion 68 of the ultrasonic treatment device 32 is not periaxially rotated but the bone can be resected only by moving (vibrating) the treating portion in the axial direction of the probe 66. Consequently, loads that act on the housing 62 or the like through the treating portion 68 are small in a case where the bone is resected by the treating portion 68. In consequence, the ultrasonic treatment device 32 inserted into the joint cavity 136 of the knee joint 100 through the portal 104 does not noticeably vibrate. That is, in the case where the bone is resected by the treating portion 68, leaping of the treating portion 68 is not caused by a rotary motion as in the abrader burr, and hence damages of the peripheral tissue can be decreased.

In addition, the surgeon uses the ultrasonic treatment device 32 and hence does not have to use the high frequency device. When the treatment is performed by using the high frequency device, there is the fear that the surface (the bone under the cartilage) is invaded by heat. On the other hand, when the ultrasonic treatment device 32 is used, normal regions of the cartilages 112a, 114a and 118a of the femur 112, the tibia 114 and the patella 118 are less invaded by heat, and the thermal necrosis is prevented from being caused to the cartilages 112a, 114a and 118a.

Next, there will be described a method in which the surgeon uses the treatment system 10 mentioned above to excise the anterior cruciate ligament 152 under the arthroscope 22 to the patient who has the damaged region in the anterior cruciate ligament 152, and a reconstructing method of the anterior cruciate ligament 152. Additionally, here, there are treated the inflammation of the synovial membrane 134, the damaged region of the meniscus 142 or 144 and the osteochondritis dissecans (OCD) which often occur together with the damage of the anterior cruciate ligament 152.

There are prepared an instrument to form the portals 102 and 104 in the knee joint 100, and an instrument for use in a surgical treatment of reconstructing the anterior cruciate ligament 152. It is to be noted that the treating portion 68 of the ultrasonic treatment device 32 is formed into a suitable shape such as the hook type.

When the anterior cruciate ligament 152 is reconstructed, the surgeon first collects a tendon to be implanted from a hamstring (a semitendinosus muscle, or a gracilis muscle), a patellar tendon or the like and prepares a graft 156 (see FIG. 14) that replaces the anterior cruciate ligament 152. The surgeon judges a position of the patient from which the tendon to be implanted is to be collected to prepare the graft 156, depending on, for example, a patient's condition, an activity plan from now on, or the like. Various ways to consider selection of the tendon to be implanted are present, but are known, and hence descriptions thereof are omitted here.

The surgeon disposes the distal end of the arthroscope 22 in the joint cavity 136 of the knee joint 100 of the patient through the first cannula 18a. The surgeon uses the perfusion device 16 to fill the joint cavity 136 of the knee joint 100 of the patient with the saline while sucking the inside of the joint cavity. In this state, the surgeon suitably observes the inside of the joint cavity 136 of the knee joint 100 by use of the arthroscope 22.

The surgeon disposes the treating portion 68 of the ultrasonic treatment device 32 in the joint cavity 136 of the knee joint 100 of the patient through the second cannula 18b. As required, the surgeon excises the inflamed region of the synovial membrane 134 and the damaged region of the meniscus 142 or 144 as described above. In addition, the surgeon appropriately treats regions to which the osteochondritis dissecans are caused in the femur 112, the tibia 114 and the patella 118.

Figure 11A:
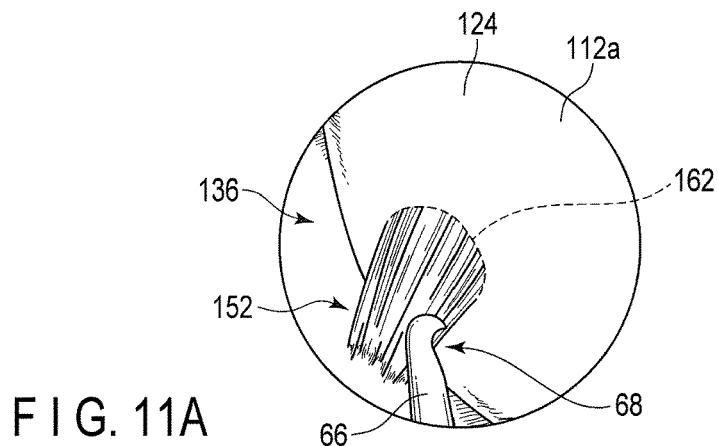
FIG. 11A is a schematic view showing a state where the ultrasonic vibration is transmitted to the treating portion of the ultrasonic treatment device to dissect the anterior cruciate ligament of a femur side of the knee joint under the arthroscope.

The arthroscope 22 passed through the first cannula 18a is moved to the posterior side of the knee joint 100, to confirm a remaining region of the anterior cruciate ligament 152 to the cartilage 112a of the lateral condyle 124 of the femur 112. As shown in FIG. 11A, the surgeon confirms a footprint region (an anatomical position to which the anterior cruciate ligament 152 adheres) 162 of the anterior cruciate ligament 152 on a femur 112 side with the arthroscope 22, and also confirms a resident ridge (bone ridge) 162a (see FIG. 11B) of the start region of the anterior cruciate ligament 152. Further, the treatment of the remaining region of the anterior cruciate ligament 152 to the cartilage 112a on the femur 112 side is performed with the ultrasonic treatment device 32. That is, as shown in FIG. 11A, the ridge 162a of the start region of the anterior cruciate ligament 152 is dissected in a state shown in FIG. 11B, by moving the treating portion 68 along the axial direction of the probe 66 while transmitting the ultrasonic vibration to the treating portion 68 of the ultrasonic treatment device 32. Specifically, as shown in FIG. 11A, the treating portion 68 of the ultrasonic treatment device 32 is disposed to abut on the remaining region of the anterior cruciate ligament 152, and the treating portion 68 is moved along the axial direction of the probe 66 while transmitting the ultrasonic vibration to the treating portion 68 of the ultrasonic treatment device 32, thereby resecting the remaining region. At this time, the treating portion 68 of the ultrasonic treatment device 32 can simultaneously cut off a soft tissue of the remaining region of the anterior cruciate ligament 152 and the hard tissue of the femur 112. In consequence, the ultrasonic treatment device 32 does not have to be replaced to the second cannula 18b.

Figure 11B:
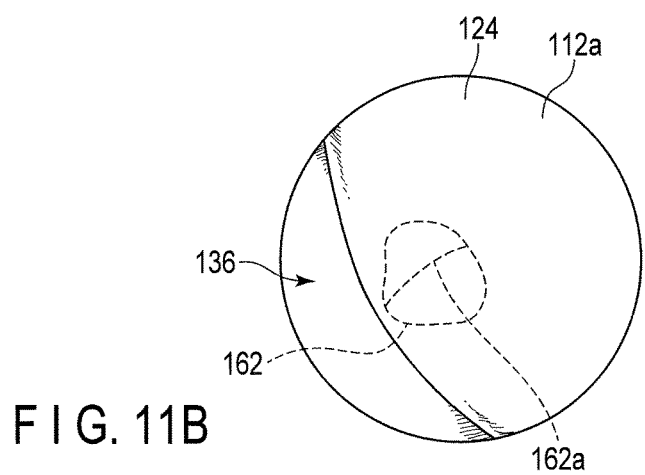
FIG. 11B is a schematic view showing a state where the ultrasonic vibration is transmitted to the treating portion of the ultrasonic treatment device to dissect the anterior cruciate ligament of the femur side of the knee joint under the arthroscope, thereby exposing a footprint region (a region to which the anterior cruciate ligament is attached)
Figure 11C:
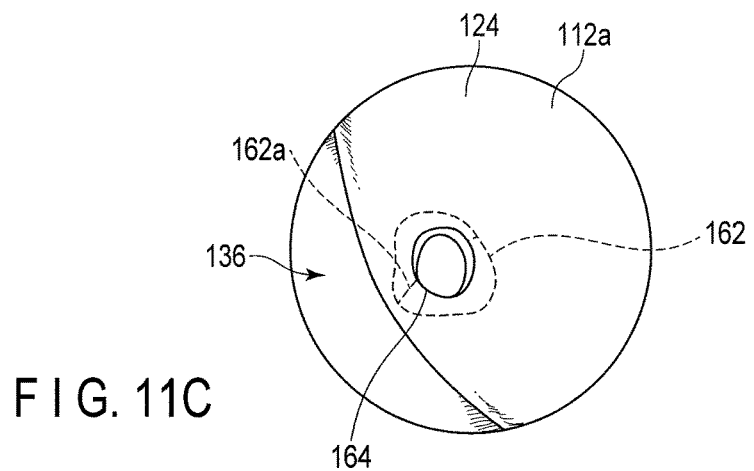
FIG. 11C is a schematic view showing a state where a concave hole (a concave region) is formed from the footprint region toward a lateral surface of a lateral condyle of the femur with the treating portion of the ultrasonic treatment device from which the ultrasonic vibration is transmitted to the footprint region of the anterior cruciate ligament of the femur side of the knee joint under the arthroscope.

As shown in FIG. 11B, a position of the footprint region 162 at which the start region of the removed anterior cruciate ligament 152 has been present is confirmed with the arthroscope 22 again. This position of the footprint region 162 is to be a position of one end of a tunnel 166 on the femur 112 side. To clarify the position of the one end of the tunnel 166, a part of the footprint region 162 of the anterior cruciate ligament 152 of the femur 112 is resected with the treating portion 68 of the ultrasonic treatment device 32 to which the ultrasonic vibration is transmitted, to form a concave hole 164 of a suitable depth shown in FIG. 11C. The surgeon uses the concave hole 164 as an auxiliary hole (a guiding hole) to form the tunnel 166 at a desirable position by an after-mentioned drill. In addition, the surgeon uses the concave hole 164 as a marking. The concave hole 164 is formed from a region to which the ligament 152 has adhered (the footprint region) toward a lateral surface of the lateral condyle 124 of the femur 112.

The probe 66 of the ultrasonic treatment device 32 can be formed into the suitable shape, and the treating portion 68 can be formed to be smaller than the shaver or the abrader burr. Consequently, in the treatment in which the ultrasonic treatment device 32 is used, the movable range to the cannula 18b can be increased, and a treatment region such as the footprint region 162 in which the start region of the anterior cruciate ligament 152 of the femur 112 has been present can more easily be approached as compared with the case where the shaver or the abrader burr is used. Additionally, the treating portion 68 of the ultrasonic treatment device 32 can simultaneously resect a remaining ligament and the femur 112. Consequently, when the surgeon performs the treatment by use of the ultrasonic treatment device 32 according to this embodiment, inserting and removing of the treatment device through the second cannula 18b, e.g., replacing of the shaver to remove the soft tissue with the abrader burr to remove the hard tissue can be eliminated.

Figure 12A:
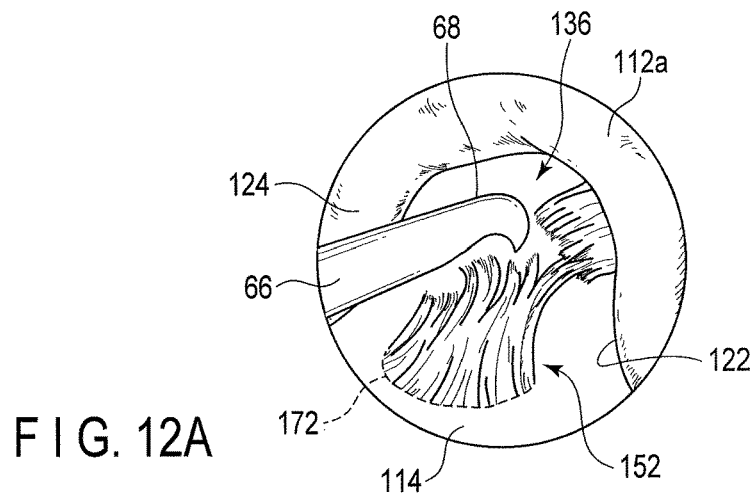
FIG. 12A is a schematic view showing a state where the ultrasonic vibration is transmitted to the treating portion of the ultrasonic treatment device to dissect the anterior cruciate ligament of a tibia side of the knee joint under the arthroscope.

Afterward, as shown in FIG. 12A, the surgeon moves the arthroscope 22 passed through the first cannula 18a to an anterior side of the knee joint 100, to confirm the remaining region of the anterior cruciate ligament 152 to the cartilage 114a on a tibia 114 side in the same manner as in the femur 112 side. As shown in FIG. 12A, the surgeon confirms a footprint region (an anatomical position to which the anterior cruciate ligament 152 adheres) 172 of the anterior cruciate ligament 152 on the tibia 114 side with the arthroscope 22. Further, a treatment of the remaining region of the anterior cruciate ligament 152 to the cartilage 114a on the tibia 114 side is performed with the ultrasonic treatment device 32. That is, as shown in FIG. 12A, the end region of the anterior cruciate ligament 152 is dissected in a state shown in FIG. 12B, by moving the treating portion 68 along the axial direction of the probe 66 while transmitting the ultrasonic vibration to the treating portion 68 of the ultrasonic treatment device 32. Specifically, as shown in FIG. 12A, the treating portion 68 of the ultrasonic treatment device 32 is disposed to abut on the remaining region of the anterior cruciate ligament 152, and the treating portion 68 is moved along the axial direction of the probe 66 while transmitting the ultrasonic vibration to the treating portion 68 of the ultrasonic treatment device 32, thereby resecting the remaining region. At this time, the treating portion 68 of the ultrasonic treatment device 32 can simultaneously cut off the soft tissue of the remaining region of the anterior cruciate ligament 152 and the hard tissue of the tibia 114. In consequence, the ultrasonic treatment device 32 does not have to be replaced to the second cannula 18b.

Figure 12B:
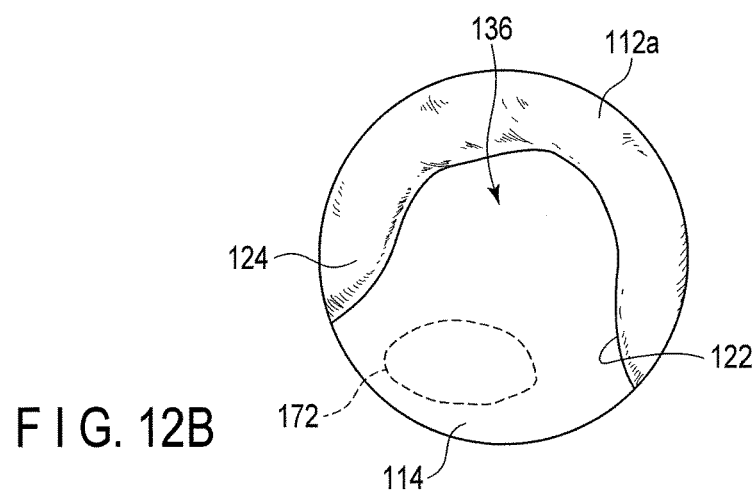
FIG. 12B is a schematic view showing a state where the ultrasonic vibration is transmitted to the treating portion of the ultrasonic treatment device to dissect the anterior cruciate ligament of the tibia side of the knee joint under the arthroscope, thereby exposing the footprint region (the region to which the anterior cruciate ligament is attached)
Figure 12C:
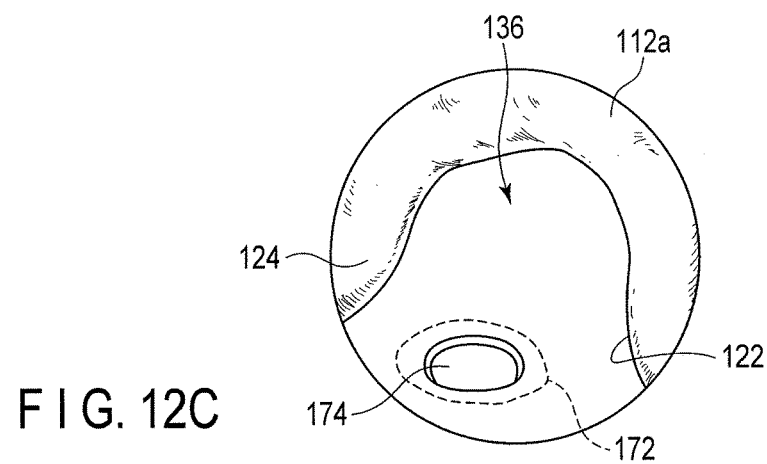
FIG. 12C is a schematic view showing a state where a concave hole (a concave region) is formed from the footprint region toward a medial side of a rough surface of the tibia with the treating portion of the ultrasonic treatment device from which the ultrasonic vibration is transmitted to the footprint region of the anterior cruciate ligament of the tibia side of the knee joint under the arthroscope.

As shown in FIG. 12B, a position of the footprint region 172 at which the end region of the removed anterior cruciate ligament 152 has been present is confirmed with the arthroscope 22 again. This position of the footprint region 172 is to be a position of one end of a tunnel 176 on the tibia 114 side. To clarify the position of the one end of the tunnel 176, the footprint region 172 of the anterior cruciate ligament 152 of the tibia 114 is resected with the treating portion 68 of the ultrasonic treatment device 32 to which the ultrasonic vibration is transmitted, to form a concave hole 174 of a suitable depth shown in FIG. 12C. The surgeon uses the concave hole 174 as an auxiliary hole (a guiding hole) to form the tunnel 176 at a desirable position by the after-mentioned drill. In addition, the surgeon uses the concave hole 174 as a marking. The concave hole 174 is formed from the region to which the ligament 152 has adhered (the footprint region) toward a medial surface of a rough surface of the tibia 114.

The ultrasonic treatment device 32 is removed from the second cannula 18b after these treatments are ended.

Figure 13A:
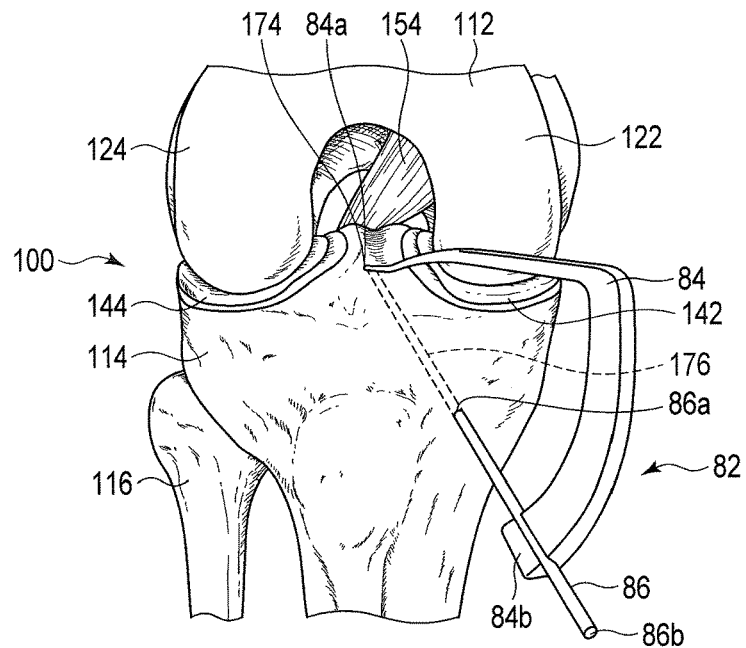
FIG. 13A is a schematic view showing a state where one end of an instrument that guides a drill to form a tunnel in a tibia is disposed in the footprint region of the anterior cruciate ligament of the tibia side of the knee joint or the concave hole formed in the footprint region, and the drill can be guided from the other end present on an outer rough surface side of the tibia toward the one end.
Figure 13B:
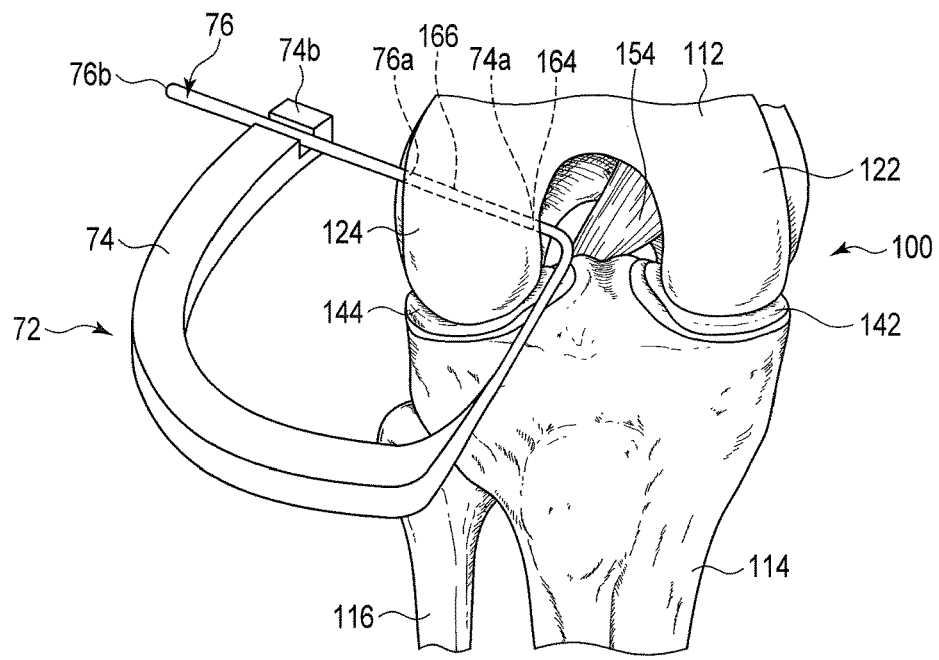
FIG. 13B is a schematic view showing a state where one end of an instrument that guides a drill to form a tunnel in a femur is disposed in the footprint region of the anterior cruciate ligament of the femur side of the knee joint or the concave hole formed in the footprint region, and the drill can be guided from the other end thereof on an outer side of the femur toward the one end.

Afterward, as shown in FIG. 13A, the surgeon forms a small hole in the tibia 114 by use of, for example, a wire-shaped first drill, and enlarges a diameter of the hole by a second drill having a larger diameter in accordance with a cross section of the graft 156 to form the tunnel 176 in the tibia 114. Similarly, as shown in FIG. 13B, the tunnel 166 is formed in the femur 112.

Here, for the purpose of forming the tunnel 166, an instrument 72 that guides the drill (not shown) is used. The instrument 72 has a main body 74 and a guiding tube 76 that guides the drill toward one end 74a of the main body 74.

The surgeon forms the concave hole 164 at one end of a position to form the bone tunnel 166 in the femur 112 with the treating portion 68 of the ultrasonic treatment device 32.

Consequently, for example, the one end 74a of the main body 74 of the instrument 72 that guides the drill to form the bone tunnel 166 is fixed to the concave hole 164 through the portal 104 from which the second cannula 18b is pulled out, immediately before the bone tunnel 166 is formed.

The guiding tube 76 of the instrument 72 is supported at the other end 74b of the main body 74. At this time, in the main body 74, a distal end 76a of the guiding tube 76 is directed toward the one end 74a of the main body 74. That is, the distal end 76a of the guiding tube 76 is disposed toward the concave hole 164. Further, the surgeon passes the guiding tube 76 supported at the other end 74b of the main body 74, in a direction from the lateral side of skin of the right knee toward the one end 74a of the main body 74. The distal end 76a of the guiding tube 76 is disposed to abut on a lateral side of the lateral condyle 124 of the femur 112. It is to be noted that, when the concave hole 164 is used as a supporting point, the distal end 76a of the guiding tube 76 is passed from a suitable position of the lateral side of the skin of the right knee, to be supported at a suitable position of the lateral side of the lateral condyle 124 of the femur 112. Further, the unshown drill is guided from a proximal end 76b of the guiding tube 76 toward the distal end 76a of the guiding tube 76. The bone tunnel 166 is formed by the drill toward the one end 74a of the main body 74 from a state where the distal end of the drill is disposed to abut on the outer side of the lateral condyle 124 of the femur 112. In consequence, the bone tunnel 166 is formed from the outer side of the skin toward the concave hole 164. At this time, the one end 74a of the main body 74 of the instrument 72 is applied to the concave hole 164 of the femur 112, and hence one end of the bone tunnel 166 is easily formed at an anatomically correct position to the femur 112. That is, the concave hole 164 of the femur 112 is used as the supporting point to form the bone tunnel (tunnel) 166 between the concave hole 164 of the femur 112 and the outer surface of the lateral condyle 124 of the femur 112. Afterward, the second drill having a larger diameter than the first drill is moved along the first drill to suitably enlarge the tunnel 166 in accordance with an outer diameter of the graft 156.

Here, for the purpose of forming the bone tunnel 176, an instrument 82 that guides the drill (not shown) is used. The instrument 82 has a main body 84 and a guiding tube 86 that guides the drill toward one end 84a of the main body 84.

In addition, the surgeon forms the concave hole 174 at one end of a position to form the bone tunnel 176 in the tibia 114 with the treating portion 68 of the ultrasonic treatment device 32. Consequently, for example, the one end 84a of the main body 84 of the instrument 82 that guides the drill to form the tunnel 176 is fixed to the concave hole 174 through the portal 104 from which the second cannula 18b is pulled out, immediately before the bone tunnel 176 is formed.

The guiding tube 86 of the instrument 82 is supported at the other end 84b of the main body 84. At this time, in the main body 84, a distal end 86a of the guiding tube 86 is directed toward the one end 84a of the main body 84. That is, the distal end 86a of the guiding tube 86 is disposed toward the concave hole 174. Further, the surgeon passes the guiding tube 86 supported at the other end 84b of the main body 84, in a direction from the lateral side of the skin of the right knee toward the one end 84a of the main body 84. The distal end 86a of the guiding tube 86 is disposed to abut on a rough surface of a front surface of the tibia 114. It is to be noted that, when the concave hole 174 is used as the supporting point, the distal end 86a of the guiding tube 86 is passed from a suitable position of the lateral side of the skin of the right knee, to be supported at a suitable position of the outer side of the rough surface of the tibia 114. Further, the unshown drill is guided from a proximal end 86b of the guiding tube 86 toward the distal end 86a of the guiding tube 86. The bone tunnel 176 is formed by the drill toward the one end 84a of the main body 84 from a state where the distal end of the drill is disposed to abut on the lateral side of the rough surface of the tibia 114. In consequence, the bone tunnel 176 is formed from the lateral side of the skin toward the concave hole 174. At this time, the one end 84a of the main body 84 of the instrument 82 is applied to the concave hole 174 of the tibia 114, and hence one end of the bone tunnel 176 is easily formed at an anatomically correct position to the tibia 114. That is, the concave hole 174 of the tibia 114 is used as the supporting point to form the bone tunnel 176 between the concave hole 174 of the tibia 114 and the rough surface of the tibia 114. Afterward, the second drill having a larger diameter than the first drill is moved along the first drill, to suitably enlarge the bone tunnel 176 in accordance with the outer diameter of the graft 156.

For example, when a position to which an end of the anterior cruciate ligament 152 has adhered is dissected by using the abrader burr, it has been difficult to form the concave hole due to the problem of accessibility or the problem that treatment time is lengthened. Here, the concave holes 164 and 174 are suitably formed by using the ultrasonic treatment device 32, and hence the one end of each of the known instruments 72 and 82 that guide the first drill to form the bone tunnels 166 and 176 can exactly be positioned. Consequently, the bone tunnels 166 and 176 can exactly be prepared more easily than before, in a state where the instrument is matched with each of the ends (the start region and the end region) of the anterior cruciate ligament 152 before damaged, to the femur 112 and the tibia 114.

Figure 14:
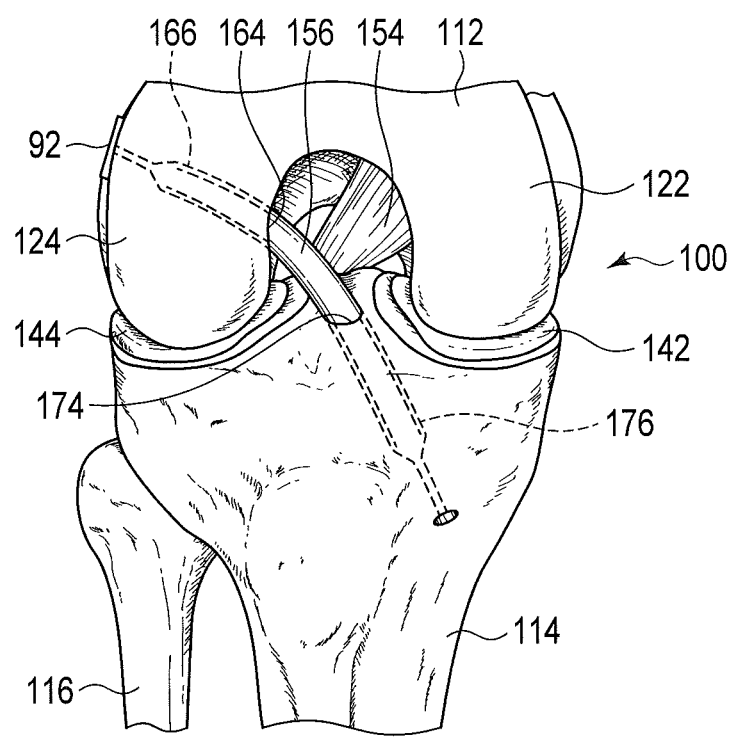
FIG. 14 is a schematic view showing a state where a graft is interposed between a tunnel on the femur side and a tunnel on the tibia side to fix end portions of the graft to outer sides of the femur and the tibia, respectively.

The instruments 72 and 82 and the like are removed, and then, as shown in FIG. 14, the graft 156 prepared in advance is inserted through the bone tunnels 166 and 176 into the joint cavity 136 of the knee joint 100, to fix the one end of the graft 156 to the lateral side of the lateral condyle 124 of the femur 112 and to fix the other end of the graft to the rough surface of the tibia 114. At this time, the graft 156 may be inserted from the femur 112 side toward the tibia 114 side, or may be inserted from the tibia 114 side toward the femur 112 side. One of the one end and the other end of the graft 156 is fixed with a fixing tool 92.

As described above, the technique of excising the damaged region of the anterior cruciate ligament 152 under the arthroscope 22 and the technique of reconstructing the anterior cruciate ligament 152 can be considered as follows.

By use of the treatment system 10, a series of treatment of removing the damaged anterior cruciate ligament 152 and exposing the footprint regions 162 and 172 can be performed with the treating portion 68 of the treatment device 32, while the one ultrasonic treatment device 32 is disposed as it is in the second cannula 18b. The surgeon has heretofore replaced and used different instruments to the portal 104 by, for example, using the shaver or the like in a removing treatment of the remaining ligament of the anterior cruciate ligament 152 and using the abrader burr or the like in the smoothening treatment (the exposing treatment) of the footprint regions 162 and 172 of the hard tissue. When the remaining ligament of the anterior cruciate ligament 152 and the treatment object regions of the footprint regions 162 and 172 are removed, the ultrasonic treatment device 32 does not have to be replaced to the portal 104. These treatments can be performed with the one ultrasonic treatment device 32.

Consequently, during the surgical treatment, the surgeon does not have to replace the treatment device 32 disposed in the joint cavity 136, and hence the surgical treatment time can be shortened.

In addition, the footprint regions 162 and 172 are dissected, and simultaneously, the concave holes 164 and 174 can be formed with the treating portion 68 of the ultrasonic treatment device 32 without replacing the tool. In consequence, the one end of each of the instruments 72 and 82 to suitably form the bone tunnels 166 and 176 can easily be positioned to the concave holes 164 and 174.

When the bone tunnels 166 and 176 are formed by utilizing the concave holes 164 and 174 prepared by using an ultrasonic output under the arthroscope 22, shift of the one end of each of the instruments 72 and 82 can be prevented, and hence the bone tunnels 166 and 176 can more exactly be prepared at the correct positions. At this time, the concave holes 164 and 174 are prepared and the concave holes 164 and 174 are utilized, and hence the bone tunnels 166 and 176 can be formed at the correct positions without necessarily using an X-ray.

The probe 66 of the ultrasonic treatment device 32 can be formed into the suitable shape, and the treating portion 68 can be formed to be smaller than the shaver or the abrader burr. Consequently, in the treatment in which the ultrasonic treatment device 32 is used, the movable range to the cannula 18b can be increased, and a treatment region such as the rear side of the knee joint 100 can more easily be approached as compared with the case where the shaver or the abrader burr is used. Additionally, in the treatment of the ultrasonic treatment device 32, the more precise and smoother treated surface can be formed than in the case where the shaver or the abrader burr is used. Consequently, when the surgeon performs the treatment by use of the ultrasonic treatment device 32 and then the patient bends and stretches the knee joint 100 to move the femur 112, the tibia 114 and the patella 118, the femur 112, the tibia 114 and the patella 118 can be prevented from being stuck on one another, which can contribute to the smooth joint movement.

The abrader burr abrades the bone that is the hard tissue by the periaxial rotation, and hence the loads that act on the abrader burr increase in a case where the bone is abraded. Consequently, the abrader burr might noticeably entirely be vibrated by the loads onto the treating portion. On the other hand, the treating portion 68 of the ultrasonic treatment device 32 is not periaxially rotated but the bone can be resected only by moving (vibrating) the treating portion in the axial direction of the probe 66. Consequently, the loads that act on the housing 62 or the like through the treating portion 68 are small in a case where the bone is resected by the treating portion 68. In consequence, the ultrasonic treatment device 32 inserted into the joint cavity 136 of the knee joint 100 through the portal 104 does not noticeably vibrate. That is, in the case where the bone is resected by the treating portion 68, the leaping of the treating portion 68 is not caused by the rotary motion as in the abrader burr, and hence the damages of the peripheral tissue can be decreased.

In addition, the surgeon uses the ultrasonic treatment device 32 and hence does not have to use the high frequency device. When the treatment is performed by using the high frequency device, there is the fear that the surface is invaded by heat. On the other hand, when the ultrasonic treatment device 32 is used, the normal regions of the cartilages 112a and 114a of the femur 112 and the tibia 114 are less invaded by heat, and the thermal necrosis is prevented from being caused to the cartilages 112a and 114a.

It is to be noted that the concave holes 164 and 174 do not necessarily have to be formed. When the concave hole 164 is not formed, one end of the instrument 72 that guides the drill to form the bone tunnel 166 is disposed in the footprint region 162 of the anterior cruciate ligament 152 of the femur 112, to form the bone tunnel 166 in the femur 112. That is, the footprint region 162 is used as the supporting point in place of the concave hole 164, to form the bone tunnel 166 in the femur 112 by use of the instrument 72. Similarly, when the concave hole 174 is not formed, one end of the instrument 82 that guides the drill to form the bone tunnel 176 is disposed in the footprint region 172 of the anterior cruciate ligament 152 of the tibia 114, to form the bone tunnel 176 in the tibia 114. That is, the footprint region 172 is used as the supporting point in place of the concave hole 174, to form the bone tunnel 176 in the tibia 114 by use of the instrument 82.

Here, an order to prepare the bone tunnels 166 and 176 is described in order of the femur 112 and the tibia 114, but, needless to say, the order may be reversed, i.e., the order may be the tibia 114 and then the femur 112.

In addition, here, there is described the example where the anterior cruciate ligament 152 is reconstructed, but also when the posterior cruciate ligament 154 is reconstructed, the treating portion 68 of the ultrasonic treatment device 32 can similarly simultaneously cut off the soft tissue of the remaining region of the posterior cruciate ligament and the hard tissue of the femur 112. In consequence, the footprint region of the posterior cruciate ligament 154 on the femur 112 side can easily be confirmed by using the arthroscope 22. Similarly, the treating portion 68 of the ultrasonic treatment device 32 can simultaneously cut off the soft tissue of the remaining region of the posterior cruciate ligament 154 and the hard tissue of the tibia 114. In consequence, the footprint region of the posterior cruciate ligament 154 on the tibia 114 side can easily be confirmed by using the arthroscope 22. In addition, the concave holes 164 and 174 can easily be formed under the arthroscope 22 by moving the treating portion 68 along the axial direction of the probe 66 while transmitting the ultrasonic vibration to the treating portion 68 of the ultrasonic treatment device 32, to the footprint regions of the posterior cruciate ligaments 154 of the femur 112 and the tibia 114 in the same manner as in the footprint regions 162 and 172 of the anterior cruciate ligament 152.

Figure 15:
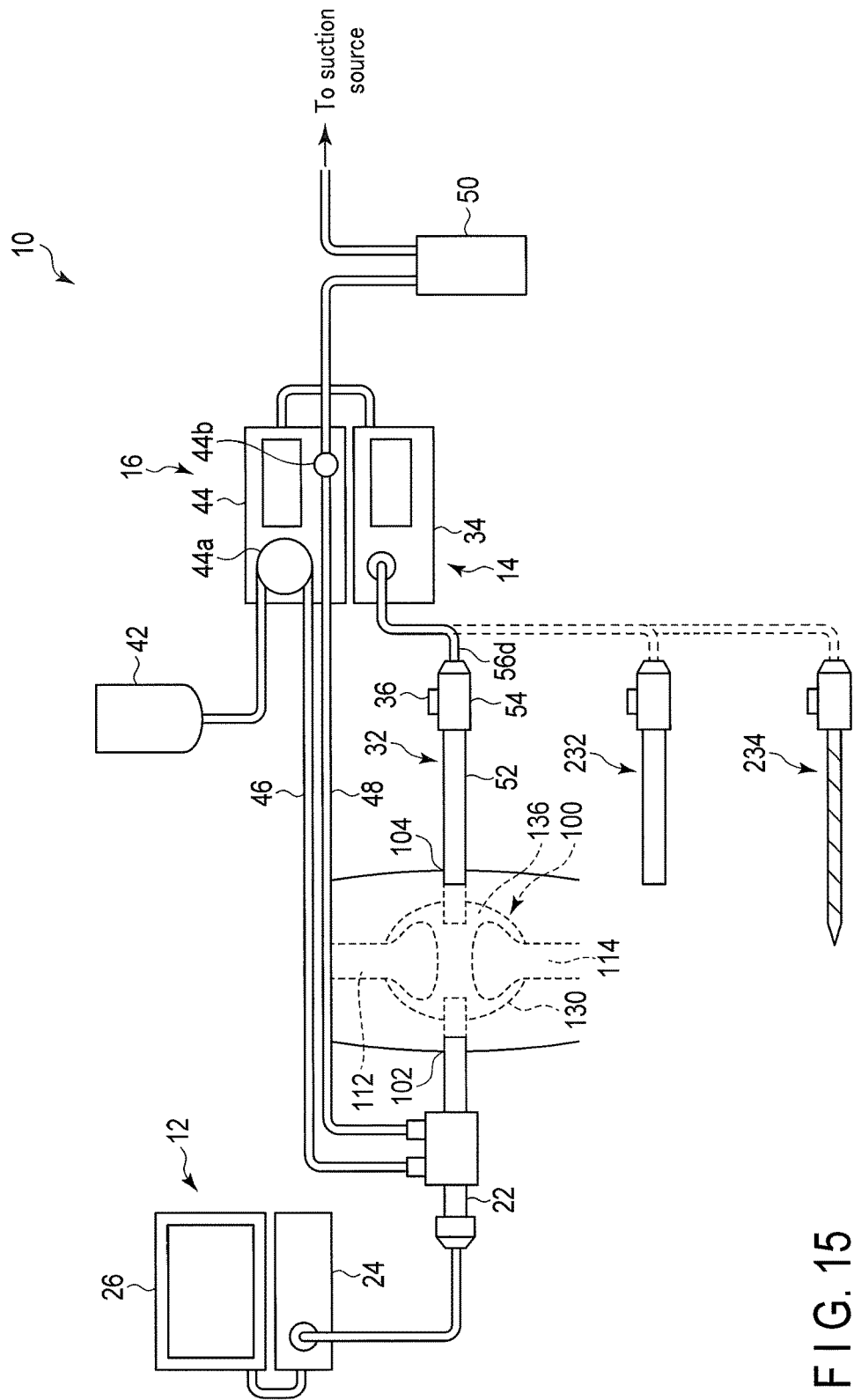
FIG. 15 is a schematic view showing a treatment system for use in a surgical treatment of a knee joint.

Next, there will be described an example where a procedure of reconstructing the anterior cruciate ligament 152 is performed. Here, the treatment device 14 of the treatment system 10 has an ultrasonic treatment unit 232 and a drill 234 shown as another treatment instrument in FIG. 15, in addition to the treatment device 32 shown in FIG. 2.

Figure 16:
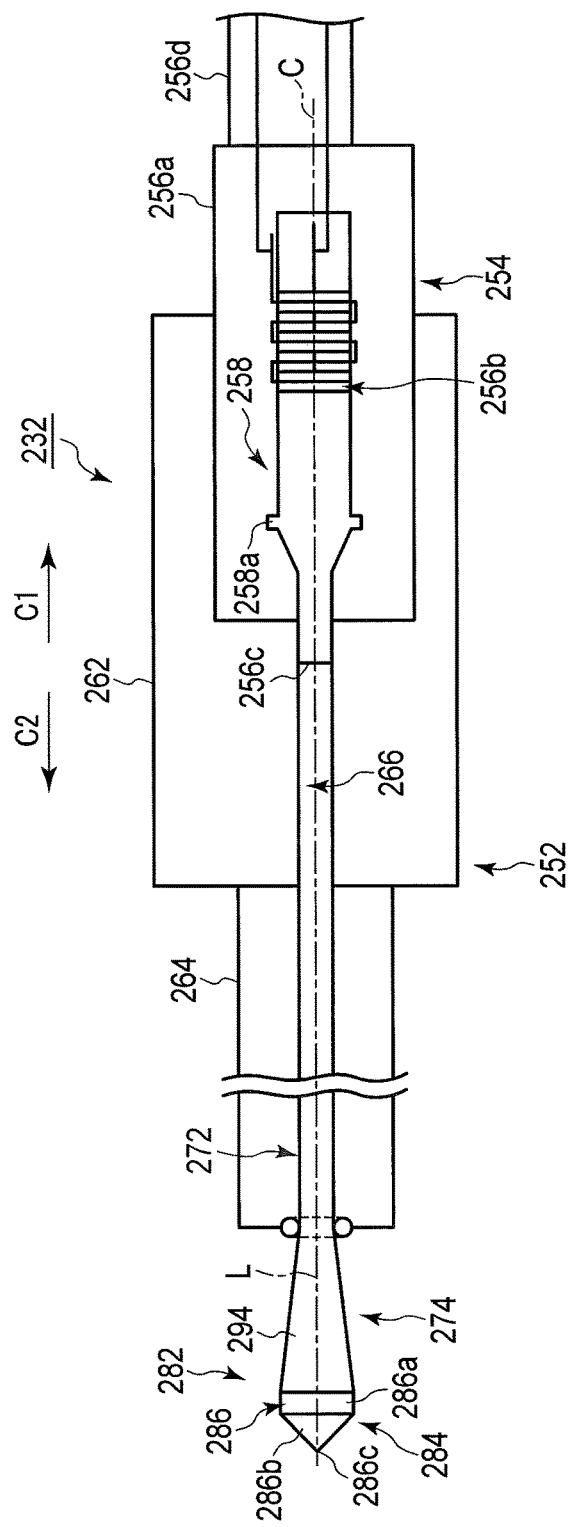
FIG. 16 is a schematic view showing one example of an ultrasonic treatment unit for use in the system shown in FIG. 15.

As shown in FIG. 16, the treatment unit 232 has an ultrasonic treatment instrument 252 and an ultrasonic transducer unit 254. It is preferable that the ultrasonic transducer unit 254 is attachable to and detachable from the ultrasonic treatment instrument 252, but the unit may be integrated with the ultrasonic treatment instrument. The ultrasonic transducer unit 254 has a housing (a transducer case) 256a, a bolt-clamped Langevin-type transducer 256b, and a connecting portion 256c at a proximal end of a later-described ultrasonic probe 266. The connecting portion 256c is formed at a distal end of the transducer 256b. It is preferable that the connecting portion 256c projects along a central axis C of the ultrasonic transducer unit 254 toward a distal side of the housing 256a. A cable 256d having one end connected to the transducer 256b and the other end connected to the controller 34 extends out from a proximal end of the housing 256a of the ultrasonic transducer unit 254. The transducer 256b and the connecting portion 256c form an integrated vibrating body 258.

The housing 256a supports a supported portion 258a of the vibrating body 258. The ultrasonic transducer unit 254 is known thus a detailed description is omitted. In a state where vibration is generated in the transducer 256b, the connecting portion 256c and a proximal end of the transducer 256b constitute antinodes of the vibration. It is to be noted that although not shown in FIG. 15, a switch 236 is preferably disposed in the housing 256a of the ultrasonic transducer unit 254 or in a later-described housing 262 of the ultrasonic treatment instrument 252.

The ultrasonic treatment instrument 252 has the housing (a handle) 262, a tubular body (an outer tube) 264 extending out from the housing 262 along the central axis C, and the ultrasonic probe 266 inserted into the tubular body 264. Here, in the ultrasonic treatment instrument 252, a side on which the housing 262 is positioned relative to the tubular body 264 is defined as a proximal side (an arrow C1 side), and a side opposite to the proximal side is defined as a distal side (an arrow C2 side). The tubular body 264 is attached to the housing 262 from the distal side. Furthermore, the ultrasonic treatment instrument 252 has a later-described treatment portion 274 in a portion on the distal side to the tubular body 264.

The housing 262 and the tubular body 264 of the ultrasonic treatment instrument 252 are made of a material having insulating properties. The housing 256a of the ultrasonic transducer unit 254 is attachably/detachably connected to the housing 262 of the ultrasonic treatment instrument 252. It is also preferable that the housing 262 of the ultrasonic treatment instrument 252 and the housing 256a of the ultrasonic transducer unit 254 are integrated.

A rotary knob (not shown) of a rotary operating member may be attached to the housing 262 of the treatment instrument 252. The rotary knob is rotatable relative to the housing 262 in a periaxial direction of the central axis of the tubular body 264. By the rotation of the rotary knob, the housing 256a of the ultrasonic transducer unit 254, the tubular body 264, the later-described treatment portion 274 and a probe main body portion 272 rotate together relative to the housing 262 in the periaxial direction of the central axis C of the probe main body portion 272.

Outer peripheral surfaces of the housing 262 and the tubular body 264 of the ultrasonic treatment instrument 252 have insulating properties. The ultrasonic probe 266 is made of a material that is capable of transmitting the ultrasonic vibration, e.g., a metal material such as a titanium alloy material. At the proximal end of the probe 266 there is fixed the connecting portion 256c of the ultrasonic transducer unit 254 that is fixed to the housing 262. It is preferable that a total length of the probe 266 is, for example, an integer multiple of a half-wave length based on a resonance frequency of the transducer 256b. The total length of the probe 266 is not limited to the integer multiple of the half-wave length based on the resonance frequency of the transducer 256b, and is suitably adjusted in accordance with the material, an amplitude enlargement ratio, or the like. Therefore, the total length of the probe 266 may be an approximate integer multiple of the half-wave length based on the resonance frequency of the transducer 256b. In the vibrating body 258 and the probe 266, materials or lengths thereof are suitably set to vibrate as a whole at the resonance frequency of the transducer 256b and a frequency in an output of the controller 34.

Figure 17A:
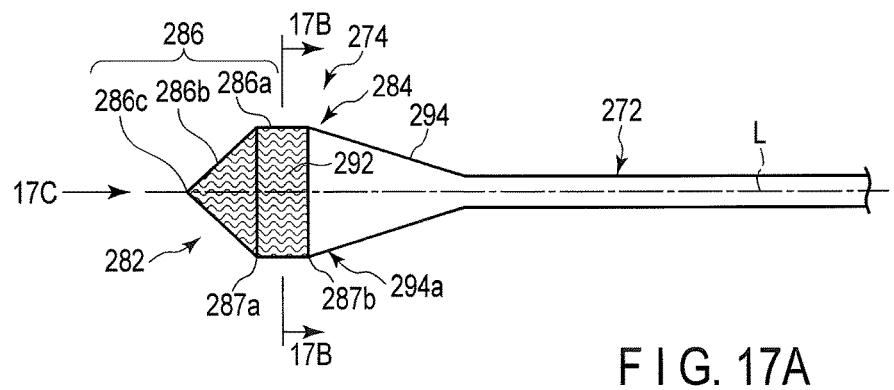
FIG. 17A is a schematic view showing an ultrasonic probe of a treatment instrument shown in FIG. 16.

As shown in FIG. 16 and FIG. 17A, the ultrasonic probe 266 has the probe main body portion 272, and has the treatment portion 274 that is disposed on the distal side of the probe main body portion 272 and that is capable of forming a hole in a bone of a treatment object by the ultrasonic vibration. The ultrasonic vibration generated in the ultrasonic transducer 256b is transmitted to the probe main body portion 272 via the connecting portion 256c of the vibrating body 258. The ultrasonic vibration generated in the transducer 256b is transmitted to the treatment portion 274 via the connecting portion 256c and the probe main body portion 272.

It is preferable that the probe main body portion 272 is formed straight. It is preferable that the treatment portion 274 extends straight out from a distal end of the probe main body portion 272 on the distal side, but the treatment portion 274 may suitably be bent in consideration of visibility of the treatment portion to the arthroscope 22. Therefore, the central axis C of the probe main body portion 272 may match a longitudinal axis L of the treatment portion 274 or may be different therefrom.

The treatment portion 274 has a cutting portion 282. As a projection shape when the proximal side is seen from the distal side along the longitudinal axis L of the treatment portion 274, the cutting portion 282 has a polygonal shape such as a rectangular shape shown in FIG. 17B and FIG. 17C or an elliptical shape (including an approximately elliptical shape) shown in FIG. 17D and FIG. 17E. The projection shape may be an approximately polygonal shape close to the elliptical shape. The polygonal shape may be a regular polygon. The projection shape may be an approximately polygonal shaped rectangle having round corners, or an approximately elliptical shape such as a track shape of an athletic field. For this reason, the projection shape is formed into a suitable shape such as the polygonal shape, the approximately polygonal shape, the elliptical shape, or the approximately elliptical shape.

As shown in FIG. 18A, the cutting portion 282 of the treatment portion 274 is moved so that the treatment portion 274 applies a force F to a bone B on the distal side along the longitudinal axis L in a state where the ultrasonic vibration is transmitted to the probe main body portion 272. Because of this, the probe 266 is moved straight or generally straight to the distal side along the central axis C. At this time, the bone is resected with the treatment portion 274.

The cutting portion 282 has a block body 286 in a distal portion of the treatment portion 274. The block body 286 is formed into a block shape to determine an outer shape (a contour of the hole) when the bone B is resected. The block body 286 has a pillar-shaped portion 286a, and a convex portion 286b projecting out from the pillar-shaped portion 286a to the distal side along the longitudinal axis L. The pillar-shaped portion 286a is formed into a shape of a pillar such as a polygonal pillar or an elliptical pillar. The pillar-shaped portion 286a and the convex portion 286b are integrally formed by cut processing or the like.

A cross section of the pillar-shaped portion 286a of the block body 286 of the cutting portion 282, which is perpendicular to the longitudinal axis L, is formed into the same shape or approximately the same shape from a distal end 287a to a proximal end 287b along the longitudinal axis L. An outer peripheral surface of the pillar-shaped portion 286a is continuous with the proximal side of the distal end 287a of the pillar-shaped portion 286a along the longitudinal axis L. Therefore, the cross section of the pillar-shaped portion 286a, which is perpendicular to the longitudinal axis L, is formed into the same area or approximately the same area from the distal end 287a to the proximal end 287b. The distal end 287a of the pillar-shaped portion 286a determines a maximum outer shape region (the contour of the hole) when the bone B is resected. The outer peripheral surface of the pillar-shaped portion 286a has the same projection shape as the projection shape of the cutting portion 282 when its proximal side is seen from the distal side along the longitudinal axis L of the treatment portion 274. In this way, the cutting portion 282 of the treatment portion 274 is formed in accordance with a shape of the hole to be formed by resecting the bone B (see FIG. 18B).

A polygonal pillar of the pillar-shaped portion 286a is formed into a suitable shape or a shape close to the suitable shape, e.g., a triangular pillar, a quadrangular pillar, a pentangular pillar, a hexagonal pillar or the like. In the pillar-shaped portion 286a, distinct corners do not necessarily have to be formed. Furthermore, the distal end 287a of the pillar-shaped portion 286a does not have to be a regular polygon, and is also preferably formed to be flat. Therefore, the hole can be formed into a desired shape by use of the probe 266 according to the present embodiment.

Figure 17B:
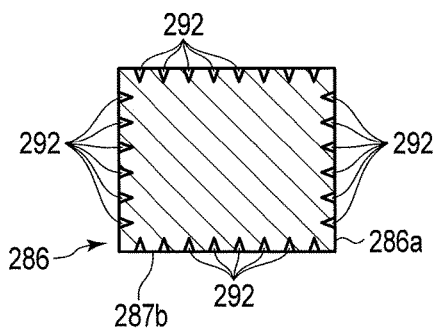
FIG. 17B is a cross-sectional view showing a state where the ultrasonic probe shown in FIG. 17A is cut along the 17B-17B line perpendicular to a longitudinal axis in FIG. 17A.
Figure 17C:
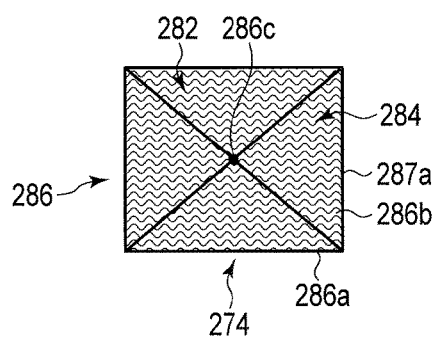
FIG. 17C is a schematic view showing a state where the ultrasonic probe shown in FIG. 17A is seen from a direction indicated by an arrow 17C in FIG. 17A.
Figure 17D:
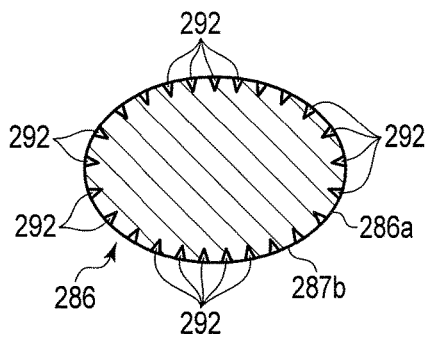
FIG. 17D is a cross-sectional view showing a modification of the ultrasonic probe shown in FIG. 17A and cut along the 17B-17B line perpendicular to the longitudinal axis in FIG. 17A.
Figure 17E:
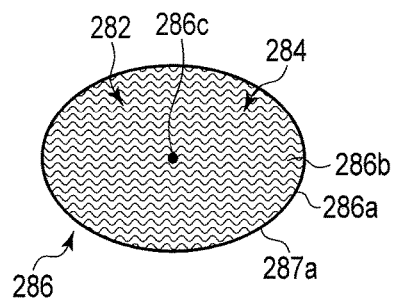
FIG. 17E is a schematic view showing a modification of the ultrasonic probe shown in FIG. 17A and seen from the direction indicated by the arrow 17C in FIG. 17A.

It is preferable that the projection shape of the cutting portion 282 is a polygonal shape such as an approximately rectangular shape shown in FIG. 17B and FIG. 17C, or the elliptical shape shown in FIG. 17D and FIG. 17E. In a case of performing reconstruction of the anterior cruciate ligament 152 (see FIG. 5) by use of a later-described STG tendon 312 (see FIG. 21), an outer shape of a cross section of the STG tendon 312 which is perpendicular to the longitudinal axis is formed as an approximately rectangular shape of about 4 mm×5 mm. Because of this, in a case where, as one example, the projection shape of the cutting portion 282 is an approximately rectangular shape, it is preferable that a size of the outer shape of the cross section perpendicular to the longitudinal axis L is, for example, about 4 mm×5 mm.

The convex portion 286b is formed on the distal side of the pillar-shaped portion 286a. The convex portion 286b projects out from the distal end 287a of the pillar-shaped portion 286a to the distal side along the longitudinal axis L, and is formed into a conical shape or an approximately conical shape based on the projection shape of the cutting portion 282. A top portion 286c of the convex portion 286b of the cutting portion 282 is formed at a suitable position on the distal side along the longitudinal axis L to the pillar-shaped portion 286a. The top portion 286c of the convex portion 286b of the cutting portion 282 is formed in a range of a projection shape of a boundary (the distal end 287a of the pillar-shaped portion 286a) between the convex portion 286b of the cutting portion 282 and the pillar-shaped portion 286a thereof when the proximal side is seen from the distal side along the longitudinal axis L. A line connecting one point of the boundary between the convex portion 286b of the cutting portion 282 and the pillar-shaped portion 286a of the cutting portion 282 to the top portion 286c may be a straight line or a curved line. Therefore, the convex portion 286b of the cutting portion 282 is not limited to the conical shape and may have the approximately conical shape. Furthermore, the top portion 286c does not have to be sharpened and may have an obtuse shape.

Here, it is defined that the convex portion 286b of the cutting portion 282 is formed as a quadrangular pyramid shown in FIG. 17C. A contact area between the top portion 286c of the convex portion 286b of the cutting portion 282 and the bone is small in an initial state when the bone is resected. Because of this, the bone can start to be cut in a state where friction between the cutting portion 282 and the bone is decreased.

Here, the top portion 286c at the topmost end of the convex portion 286b of the cutting portion 282 is appropriately sharp. When the top portion 286c is brought into contact with or pressed onto the bone B with suitable force, it is difficult for the top portion to slip to the bone B as compared with the obtuse shape. For this reason, when the ultrasonic vibration is transmitted to the probe 266 in the state where the top portion 286c is brought into contact with or pressed onto the bone B with suitable force, it is difficult for the top portion to slip to the bone B, and for the position to shift in a case where a hole 300 (see FIG. 18A and FIG. 18B) starts to be opened. Therefore, when the top portion 286c is appropriately sharp, it is difficult for the position of the top portion 286c at the topmost end of the convex portion 286b of the cutting portion 282 to shift to the bone B, and it becomes easy to determine a position at which the hole 300 is to be formed.

As shown in FIG. 17A to FIG. 17C, the treatment portion 274 has a discharging portion 284 to discharge cutting debris of the bone resected by the cutting portion 282 from the cutting portion 282 toward the proximal side along the longitudinal axis L. A part of the discharging portion 284 is disposed in the cutting portion 282. The discharging portion 284 has concave portions 292 formed in an outer peripheral surface of the cutting portion 282 and a shaft portion 294 disposed on the proximal side of the cutting portion 282.

As shown in FIG. 17B, in the outer peripheral surface of the cutting portion 282, there are formed the concave portions 292 of the discharging portion 284 that decreases the contact area between the treatment portion 274 and the bone, and which becomes a discharge path of the cutting debris. Here, each of the concave portions 292 is formed into a wavelike shape having a bottom surface at a position dented to outer peripheral surfaces of the pillar-shaped portion 286a and the convex portion 286b. The bottom surface of the concave portion 292 is closer to the central axis C (the longitudinal axis L) than the pillar-shaped portion 286a. The concave portions 292 do not necessarily have to be formed in the convex portion 286b (see FIG. 19A).

The shaft portion 294 is extended from the block body 286 of the cutting portion 282 to the proximal side along the longitudinal axis L. The shaft portion 294 is interposed between the distal end of the probe main body portion 272 and the proximal end 287b of the block body 286 of the cutting portion 282. A projection shape of the shaft portion 294 when its proximal side is seen from the distal side along the longitudinal axis L falls within a range of a projection shape of the block body 286 of the cutting portion 282.

The shaft portion 294 has a distal portion 294a that is continuous with a proximal end of the block body 286. In the distal portion 294a of the shaft portion 294, a cross-sectional area of a cross section perpendicular to the longitudinal axis L decreases from the distal side toward the proximal side along the longitudinal axis L. The shaft portion 294 also has a range in which the cross-sectional area of the cross section perpendicular to the longitudinal axis L increases from the distal side toward the proximal side, or is maintained to be constant in a range on the proximal side of the distal portion 294a. That is, the shaft portion 294 has a narrowed range between its distal end and its proximal end. A boundary between the distal portion 294a of the shaft portion 294 and the proximal end of the block body 286 (the distal end 287a of the pillar-shaped portion 286a) has a shape to prevent stress concentration in a state where the ultrasonic vibration is transmitted. Therefore, a boundary between the distal portion 294a of the shaft portion 294 and the proximal end 287b of the pillar-shaped portion 286a of the block body 286 is smoothly continuous. Note that when the treatment portion 274 is seen from the distal side toward the proximal side along the longitudinal axis L, the shaft portion 294 is hidden behind the block body 286 and cannot be observed. Therefore, the shaft portion 294 that is continuous with the proximal side of the block body 286 can be a part of the discharging portion 284 to discharge the cutting debris of the bone or a liquid such as an irrigation liquid to the proximal side along the longitudinal axis L.

When the treatment portion 274 is seen from the distal side to the proximal side in a direction indicated by arrow 17C in FIG. 17A, in other words along the longitudinal axis L, outer shapes of the convex portion 286b of the cutting portion 282 and the pillar-shaped portion 286a thereof are observed as an outer shape of the treatment portion 274 as shown in FIG. 17C. At this time, the concave portions 292 of the discharging portion 284 are formed in the pillar-shaped portion 286a, but in an outer edge of the treatment portion 274 in FIG. 17C, the outer peripheral surface of the pillar-shaped portion 286a appears at least once between the distal end 287a of the pillar-shaped portion 286a and the proximal end 287b thereof. Therefore, the cutting portion 282 determines the maximum outer shape region. Accordingly, when the proximal side is seen from the distal side along the longitudinal axis L, the projection shape of the cutting portion 282 forms the shape of the hole when the bone B is resected by using the treatment instrument 252.

The concave hole 300 of the desired shape has, for example, an opening edge 302 of the same shape and size as in the projection shape of the cutting portion 282 of the treatment portion 274 when the proximal side is seen from the distal side along the longitudinal axis L, and the concave hole is dented straight to an inner side in the same shape as the shape of the opening edge 302. Therefore, one example of the desired shape of the hole 300 is a rectangular shape having a suitable depth.

Next, an operation of the treatment system 10 according to this embodiment will be described. Here, mainly an operation of the ultrasonic probe 266 of the treatment unit 232 will be described when performing the reconstruction of the anterior cruciate ligament in a case where the concave hole 300 is formed in the bone B.

The ultrasonic transducer unit 254 is attached to the ultrasonic treatment instrument 252 to form the treatment unit 232. At this time, the proximal end of the ultrasonic probe 266 is connected to the connecting portion 256c of the ultrasonic transducer unit 254. Here, for the purpose of simplifying the description, it is defined that the central axis C of the probe main body portion 272 matches the longitudinal axis L of the treatment portion 274.

When the switch 36 is operated, the controller 34 supplies energy to the ultrasonic transducer 256b of the vibrating body 258 fixed to the proximal end of the ultrasonic probe 266, to generate the ultrasonic vibration in the ultrasonic transducer 256b. Because of this, the ultrasonic vibration is transmitted to the ultrasonic probe 266 via the vibrating body 258. This vibration is transmitted from the proximal end of the ultrasonic probe 266 toward the distal side. At this time, the connecting portion 256c at the distal end of the vibrating body 258 and a proximal end of the vibrating body 258 are antinodes of the vibration. One point on the central axis C on an inner side of the supported portion 258a is a node of the vibration. The proximal end of the ultrasonic probe 266, which is connected to the connecting portion 256c of the vibrating body 258, is an antinode of the vibration, and the cutting portion 282 of the treatment portion 274 is an antinode of the vibration.

The cutting portion 282 of the treatment portion 274 is the antinode of the vibration, so the cutting portion is displaced along the longitudinal axis L at a rate (e.g., several thousand m/s) based on the resonance frequency of the transducer 256b. Therefore, when the treatment portion 274 is pressed onto the bone B toward the distal side along the longitudinal axis L in the state where the vibration is transmitted, a region of the bone B which is in contact with the treatment portion 274 is shattered. Consequently, in the bone B, the concave hole 300 is formed along the longitudinal axis L of the treatment portion 274 of the ultrasonic probe 266.

Here, the top portion 286c at the topmost end of the convex portion 286b of the cutting portion 282 is appropriately sharp. When the top portion 286c is brought into contact with or pressed onto the bone B with suitable force, it is difficult for the top portion 286c to slip to the bone B as compared with the obtuse shape. Because of this, when the ultrasonic vibration is transmitted to the probe 266 in the state where the top portion 286c is brought into contact with or pressed onto the bone B with suitable force, it is difficult for the top portion to slip to the bone B and to shift in the case of starting opening the hole 300 (see FIG. 18A and FIG. 18B). Therefore, when the top portion 286c is suitably sharp, it is difficult for the position of the top portion 286c at the topmost end of the convex portion 286b of the cutting portion 282 to shift to the bone B, and it becomes easy to determine the position where the hole 300 is to be formed.

Additionally, in a case where the bone B is present under a cartilage, when the treatment portion 274 of the ultrasonic probe 266 is pressed onto the cartilage toward the distal side along the longitudinal axis L, a region of the cartilage which is in contact with the treatment portion 274 is excised by an operation of the ultrasonic vibration, and a concave hole is formed in the cartilage.

The concave portions 292 of the discharging portion 284 are respectively formed in the convex portion 286b and the pillar-shaped portion 286a of the treatment portion 274 of the ultrasonic probe 266. The concave portions 292 of the discharging portion 284 are formed whereby, in the case where the concave hole 300 is formed in the bone B, the contact area between the cutting portion 282 and the bone B is smaller than in a case where the concave portions 292 are not formed. Thus, the friction between the cutting portion 282 and the bone B is decreased to inhibit generation of frictional heat in the treatment portion 274 and the bone B. Also, due to the presence of the concave portions 292, a surface area of the cutting portion 282 increases as compared with the case where the concave portions 292 are not formed. A joint liquid or the irrigation liquid is present in the joint 100, and thus in the treatment portion 274, a heat radiation ability improves due to the presence of the concave portions 292, and the treatment portion is suitably cooled. Furthermore, the cutting debris of the bone B is disposed in the concave portions 292. The concave portions 292 are continuous from the distal end 287a of the pillar-shaped portion 286a to the proximal end 287b thereof. Because of this, the cutting debris of the bone B, once entering the concave portions 292, moves along the concave portions 292 which are continuous from the distal end 287a of the pillar-shaped portion 286a to the proximal end 287b thereof. Therefore, the cutting debris of the bone B is easily discharged to the proximal side of the treatment portion 274 through the distal end 287a of the pillar-shaped portion 286a and the proximal end 287b thereof. Thus, the treatment portion 274 of the treatment unit 232 is capable of containing the concave hole 300 at the suitable rate.

When the proximal side of the treatment portion 274 is seen from the distal side along the longitudinal axis L, the shaft portion 294 of the discharging portion 284 cannot be observed due to the presence of the pillar-shaped portion 286a of the cutting portion 282. Therefore, when forming the concave hole 300, a space is formed between the proximal end 287b of the pillar-shaped portion 286a, the shaft portion 294, and a lateral surface of the bone hole 300. Therefore, the cutting debris of the bone B is discharged from the proximal end 287b of the pillar-shaped portion 286a toward the space between the shaft portion 294 and the lateral surface of the bone hole 300.

In this way, the cutting debris of a region of the bone B which is treated with the treatment portion 274 is discharged to the proximal side through the concave portions 292 of the discharging portion 284 along the longitudinal axis L. In particular, the inside of the joint 100 is filled with the joint liquid. Furthermore, in the joint 100, the irrigation liquid circulates. Because of this, the joint liquid or the irrigation liquid becomes a lubricant to easily discharge the cutting debris of the bone B from the cutting portion 282 to the proximal side along the longitudinal axis L. In the case where the concave hole 300 is formed to the desired depth in the bone B, the pressed switch 36 is released to stop the generation of the ultrasonic vibration. Then, the ultrasonic probe 266 is moved to the proximal side along the longitudinal axis L.

As shown in FIG. 18B, the concave hole 300 formed in the bone B is formed into the same shape as that of an outer edge of the pillar-shaped portion 286a of the cutting portion 282 from an inlet 302 of the hole to an inner region 304. An innermost position 306 of the concave hole 300 is formed into the same shape as that of an outer shape of the convex portion 286b including the top portion 286c. That is, as shown in FIG. 18A, in a case where the ultrasonic vibration is transmitted to the probe 266 of the ultrasonic treatment instrument 252 to form the concave hole 300 in the bone B, the shape of the cutting portion 282 of the treatment portion 274 can be copied.

The pillar-shaped portion 286a of the cutting portion 282 of the probe 266 maintains a region constituting the maximum outer shape region from the distal end 287a to the proximal end 287b, and imparts a certain degree of length along the longitudinal axis L. That is, an outer shape of the pillar-shaped portion 286a from the distal end 287a toward the proximal end has a certain degree of length parallel to the longitudinal axis L. Therefore, when the probe 266 is moved straight along the longitudinal axis L, the hole 300 can be formed straight along the longitudinal axis L with the pillar-shaped portion 286a of the cutting portion 282.

The ultrasonic vibration is transmitted to the probe 266 of the treatment unit 232 according to this embodiment, and the ultrasonic vibration is applied to a region of the bone B in which the hole is to be formed, whereby the region of the bone B, which is in contact with the cutting portion 282 of the treatment portion 274 at the distal end of the probe 266, is finely shattered and cut. The distal portion of the treatment portion 274 is formed into a convex shape (the convex portion 286b), and additionally, the concave portions 292 of the discharging portion 284 to discharge the cutting debris of the bone B are formed in the cutting portion 282. For this reason, as compared with the cutting portion 282 which does not have the convex portion 286b and keeps the projection shape of the pillar-shaped portion 286a in an axial direction, the cutting portion having the convex portion 286b and the concave portions 292 of the discharging portion 284 can proceed with a hole opening processing earlier.

The cutting portion 282 is moved along the longitudinal axis L, so that the shape of the distal end 287a of the pillar-shaped portion 286a when the treatment portion 274 is seen from the distal side along the longitudinal axis L can be copied to the opening edge of the concave hole 300. Because of this, the projection shape of the cutting portion 282 along the longitudinal axis L is the same as the desired shape of the concave hole 300. The bone B is further dug with the cutting portion 282, so that the concave hole 300 having the desired shape and desired depth can be opened in the bone B.

In addition, the distal portion of the treatment portion 274 is formed into a convex shape (the convex portion 286b), and due to the concave portions 292 of the discharging portion 284, the contact area between the bone B and the cutting portion 282 decreases, whereby the cutting debris is further easily discharged to the proximal side of the cutting portion 282. Therefore, when cutting the bone B, it is possible to inhibit the generation of the frictional heat between the treatment portion 274 and the bone B and to increase a processing rate.

It is to be noted that the treatment portion 274 of the probe 266 of the ultrasonic treatment instrument 252 is not limited to the treatment portion shown in FIG. 17A, and various shapes such as the shapes shown in FIG. 19A to FIG. 20C are allowed.

Figure 19A:
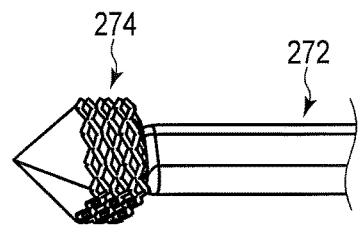
FIG. 19A is a schematic perspective view showing a modification of a treatment portion of the ultrasonic probe shown in FIG. 17A.

In an example shown in FIG. 19A, a shape of the concave portion 292 of the discharging portion 284 of the treatment portion 274 is different from that of the discharging portion 284 of the treatment portion 274 shown in FIG. 16.

Figure 19B:
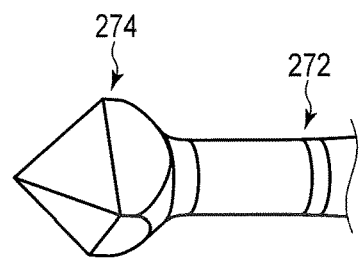
FIG. 19B is a schematic perspective view showing a modification of the treatment portion of the ultrasonic probe shown in FIG. 17A.

In an example shown in FIG. 19B, the discharging portion 284 of the treatment portion 274 is not present.

Figure 20A:
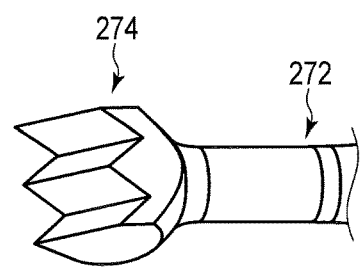
FIG. 20A is a schematic perspective view showing a modification of the treatment portion of the ultrasonic probe shown in FIG. 17A.

In an example shown in FIG. 20A, the number of the top portions 286c of the treatment portion 274 is plural (three).

Figure 20B:
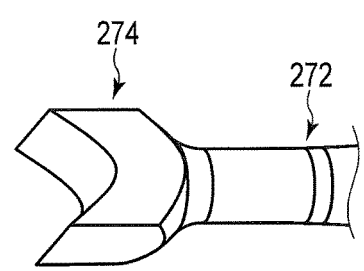
FIG. 20B is a schematic perspective view showing a modification of the treatment portion of the ultrasonic probe shown in FIG. 17A.

In an example shown in FIG. 20B, the number of the top portions 286c of the treatment portion 274 is plural (two).

Figure 20C:
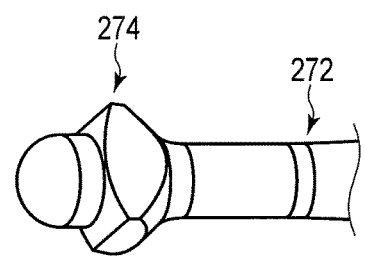
FIG. 20C is a schematic perspective view showing a modification of the treatment portion of the ultrasonic probe shown in FIG. 17A.

In an example shown in FIG. 20C, the convex portion 286b of the cutting portion 282 is formed into a hemispherical shape. It is preferable that a size of the convex portion 286b is the same as or slightly smaller than a hole diameter of a hole (a drilled hole) formed with the drill 234. In the treatment portion 274 of the example shown in FIG. 20C, the ultrasonic vibration is transmitted to the convex portion 286b inserted in the drilled hole. The convex portion 286b is guided to the drilled hole, and by use of the drilled hole as a guide hole, the hole 300 (see FIG. 18B) is formed straighter.

A surgical procedure in a case where the anterior cruciate ligament 152 is damaged is classified into, for example, two procedures in accordance with a material of an implant tendon for the ligament to be reconstructed. One is a procedure of using a semitendinosus tendon or a gracilis tendon that is present on an inner side of a knee as a implant tendon (an STG tendon) 310 shown in FIG. 21. The other procedure is a procedure of using a patellar tendon as an implant tendon (a BTB tendon) 330 shown in FIG. 23. Note that here, in any case, the bone hole 300 is formed from the inside of the joint cavity 136 toward the outside of the femur 112 by an inside out method.

A first procedure example will be described with reference to FIG. 21 and FIG. 22A to FIG. 22E. FIG. 22A to FIG. 22E schematically show a state where the femur 112, the tibia 114, and the joint cavity 136 of the knee joint 100 are seen from the anterior side. Arrows in FIG. 22A to FIG. 22D indicate a bone excising direction (a moving direction of the probe 266 along the longitudinal axis L).

Figure 21:
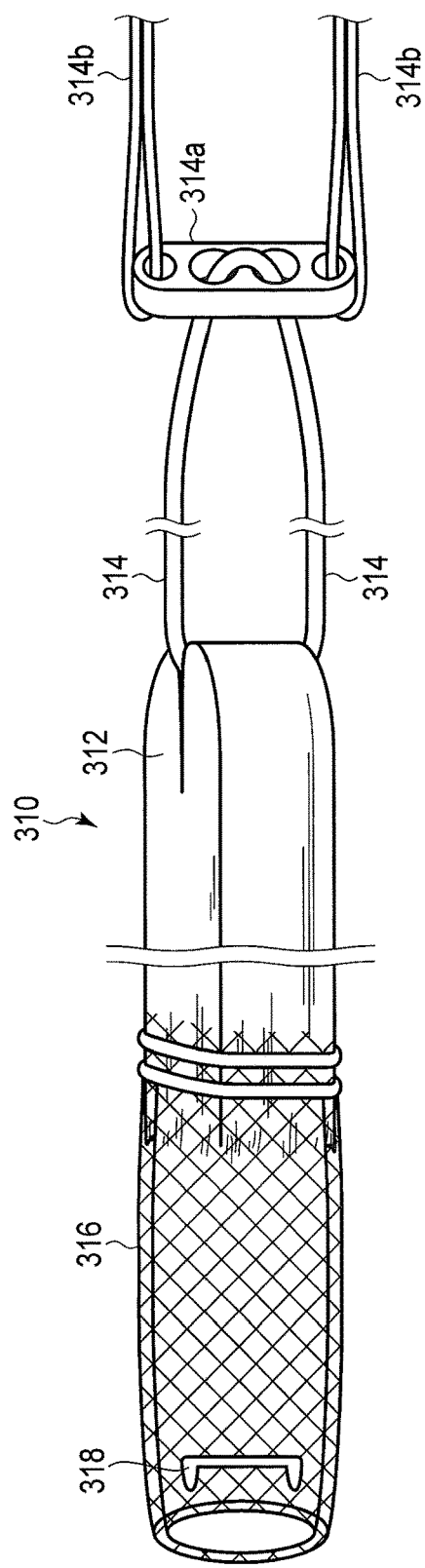
FIG. 21 is a schematic view of an implant tendon which includes an STG tendon for use in reconstruction of the anterior cruciate ligament.

Here, an example is described where the semitendinosus tendon or the gracilis tendon that is present on the inner side of the knee is used as the implant tendon. This implant tendon is referred to as the STG tendon. As shown in FIG. 21, the STG tendon as the tendon to be implanted is folded several times to be formed to a suitable length as a part of the implant tendon 310. The implant tendon 310 has the STG tendon 312, a suspension fixture 314a disposed at one end of the STG tendon 312 via suture threads 314 and, for example, a pair of artificial ligaments 316 fixed to the other end of the STG tendon 312. The artificial ligaments 316 are prepared in the form of strings made of, for example, polyester or the like. A string 314b wound around the fixture 314a is used in taking the fixture 314a from the knee joint 100 to the outside of the femur 112 through a later-described concave hole 320 and a later-described through hole 322. An outer shape of a cross section of the STG tendon 312, which is perpendicular to a longitudinal axis, is an approximately rectangular shape, an approximately elliptical shape close to a rectangular shape, or the like. Furthermore, the outer shape of the STG tendon 312 has a size of, for example, about 4 mm×5 mm. It is preferable that, among later-described bone holes 320, 322, 324, and 326, a position into which the STG tendon 312 is to be inserted has a size and a shape which conform to the outer shape of the STG tendon 312. The STG tendon 312 is preferably sampled before dissecting a region to which the damaged anterior cruciate ligament 152 adheres.

It is preferable that the implant tendon 310 is disposed in the same region as the region to which the damaged anterior cruciate ligament 152 adheres. Because of this, the region to which the damaged anterior cruciate ligament 152 adheres is dissected by using an unshown treatment unit to clarify footprint regions 162 and 172 to which the anterior cruciate ligament 152 has adhered. At this time, a suitable ultrasonic treatment instrument, an abrader, or the like are usable. Positions to form the later-described bone holes 320 and 324 to the footprint regions 162 and 172 are determined by marking or the like. A lateral cross section of the treatment portion 274 of the treatment instrument 252 mentioned above is not circular, thus the treatment portion has an orientation. Therefore, orientations of the bone holes 320 and 324 to be formed in the footprint regions 162 and 172 are also determined. Although not shown in the drawing, the footprint region 162 is present in a lateral wall posterior region of an intercondylar fossa of the femur 112. Furthermore, the footprint region 172 is present on an inner side of an anterior intercondylar area of the tibia 114.

Here, a procedure is performed using the inside-out method. To the femur 112, the treatment portion 274 of the probe 266 of the ultrasonic treatment instrument 252 is inserted from the suitable portal 104 into the joint cavity 136 of the knee joint 100. A distal end of the treatment portion 274 is disposed to face the footprint region 162. At this time, the distal end of the treatment portion 274 can be brought directly into contact with the footprint region 162. Therefore, in a case where the later-described bone hole 320 is formed, a known guide wire and a known guide are not required. Thus, a central area of a marked region of the footprint region 162 is cut from the inside of the joint 100 to the outside of the femur 112 with the treatment portion 274, to form the concave hole 320 shown in FIG. 22A straight to the femur 112. The cross section of the treatment portion 274, which is perpendicular to the longitudinal axis L of the treatment portion 274, is approximately rectangular. The ultrasonic treatment instrument 252 is pulled out from the portal 104 after the approximately rectangular concave hole 320 is formed.

A projection shape of the treatment portion 274 of the ultrasonic treatment instrument 252, when its proximal side is observed from the distal side along the longitudinal axis L, is formed to be approximately rectangular. Thus, the cross section of the pillar-shaped portion 286a of the treatment portion 274 of the ultrasonic treatment instrument 252 which is perpendicular to the longitudinal axis L has the same size and shape or about the same size and shape from the distal end 287a to the proximal end 287b. For this reason, in the state where the ultrasonic vibration is transmitted to the probe 266, the approximately rectangular parallelepiped concave hole (a second bone hole) 320 similar to the concave hole 300 shown in FIG. 18B is formed in a predetermined orientation in the marked region of the footprint region 162 shown in FIG. 18B. That is, in the state where the ultrasonic vibration is transmitted to the treatment portion 274 of the ultrasonic treatment instrument 252, the ultrasonic vibration is applied from the treatment portion 274 to the femur 112. Therefore, the bone hole 320 of the femur 112 is cut and expanded from the inside of the knee joint 100 along a predetermined depth, to form the bone hole 320 of a suitable shape which receives the implant tendon 310.

By the inside-out method, to the femur 112, the drill 234 is inserted from the suitable portal 104 into the joint cavity 136 of the knee joint 100. At this time, a distal end of the drill 234 can be inserted directly into the concave hole 320 to abut on a bottom surface of the concave hole 320. In this state, the through hole (the drilled hole) 322 shown in FIG. 22B is formed in the femur 112. In a case of forming the through hole 322, the known guide wire and guide are not required. A diameter of the through hole 322 is adjusted into such a diameter that the suspension fixture 314a can pass from a joint cavity 136 side through a cortical bone on an outer side of the femur 112. The drill 234 is pulled out from the portal 104 after the through hole 322 is formed. At this time, the distal end of the drill 234 can abut on the bottom surface of the concave hole 320, so it is easy to match a central axis of the through hole 322 with a central axis of the concave hole 320.

It is to be noted that the through hole 322 is formed with the drill 234, but it is also preferable to form the through hole with the ultrasonic treatment instrument 252. That is, the through hole 322 may be formed by applying the ultrasonic vibration from the treatment portion 274 to the femur 112 in a state where the ultrasonic vibration is transmitted to the treatment portion 274 of the ultrasonic treatment instrument 252. Namely, it is also preferable that the suitable through hole is formed with the ultrasonic treatment instrument 252.

Furthermore, for the tibia 114, a central area of a marked region of the footprint region 172 is cut from the inside of the joint 100 to the outside of the tibia 114 with the treatment portion 274 of the ultrasonic treatment instrument 252. As a result, the concave hole 324 shown in FIG. 22C is formed straight to the tibia 114. The concave hole 324 is formed similarly to the concave hole 300 shown in FIG. 18B.

Figure 22D:
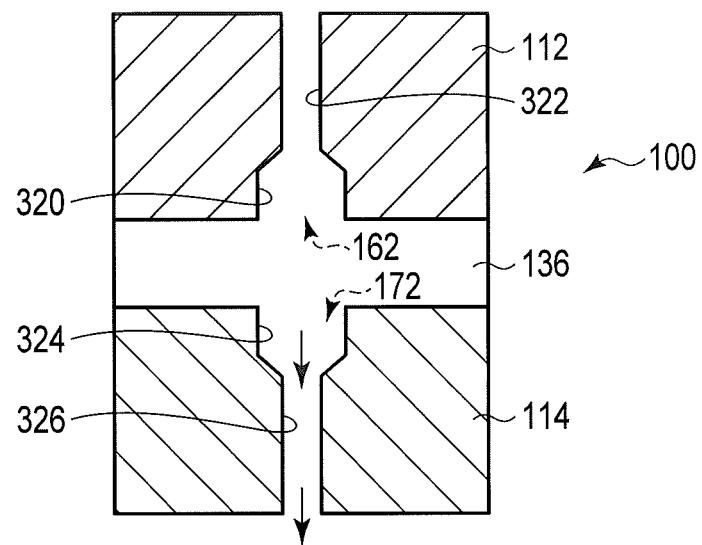
FIG. 22D is a schematic view showing a state where a through hole is formed to the concave hole of the tibia in the state shown in FIG. 22C.

To the tibia 114, the drill 234 is inserted from the suitable portal 104 into the joint cavity 136 of the knee joint 100. At this time, the distal end of the drill 234 can directly be inserted into the concave hole 324 to abut on a bottom surface of the concave hole 324. In this state, the through hole (the drilled hole) 326 shown in FIG. 22D is formed in the tibia 114. In the case of forming the through hole 326, the known guide wire and guide are not required. The drill 234 is pulled out from the portal 104 after the through hole 326 is formed.

The fixture 314a at one end of the implant tendon 310 by the STG tendon 312 is taken out from, for example, the second portal 104 to the outside of the femur 112 via the concave hole 320 and the drilled hole 322 of the femur 112. At this time, the outer shape of the STG tendon 312 is approximately rectangular as described above, thus the implant tendon 310 is disposed in accordance with the orientation of the concave hole 320. On the other hand, the other end of the implanted tendon 310 is taken out from the tibia 114 via the concave hole 324 and the drilled hole 326 of the tibia 114. Then, a tensile force of the implanted tendon 310 is suitably adjusted in accordance with a bent state of the knee joint 100 to fix the other end of the implanted tendon 310 to an outer side of the tibia 114 with a fixture 318 such as a staple (a screw may be used) (see FIG. 22E).

To these approximately rectangular concave holes 320 and 324, the STG tendon 312 of the approximately rectangular implant tendon 310 is disposed in accordance with the orientation of the concave holes 320 and 324. Thus, a clearance formed between the STG tendon 312 of the implant tendon 310 and the concave hole 320 and a clearance formed between the STG tendon 312 and the concave hole 324 becomes smaller as much as possible. Furthermore, the clearance between the STG tendon 312 and the bone is small, and thus a space volume to be regenerated as the bone in is smaller, facilitating the formation of a ligament by the STG tendon 312. Also, the clearance is decreased, whereby it is possible to decrease an amount of the joint liquid to enter the bone holes 320 and 324 and to inhibit enlargement of the bone holes 320 and 324 due to the joint liquid. Furthermore, the concave holes 320 and 324 are formed with the treatment portion 274 of the ultrasonic treatment instrument 252 having the block-shaped cutting portion 282 shown in FIG. 2, whereby the holes are not expanded with a dilator. Therefore, even in patients with low bone density, bone fracturing can be suppressed, so it is easy to perform an operation using the implant tendon 310.

The shape of the concave holes 320 and 324 is copied from the shape of the treatment portion 274 of the probe 266 of the ultrasonic treatment instrument 252 shown in FIG. 16 and FIG. 17A. Because of this, in a case where the outer shape of the cross section of the pillar-shaped portion 286a of the treatment portion 274 of the probe 266 of the ultrasonic treatment instrument 252, which is perpendicular to the longitudinal axis L, is not rectangular but is elliptical, elliptical concave holes are formed. In a case where the outer shape of the cross section of the pillar-shaped portion 286a of the treatment portion 274 of the probe 266 of the ultrasonic treatment instrument 252, which is perpendicular to the longitudinal axis L, is not rectangular but is suitably polygonal, the concave holes of the polygonal shape are formed. The shape of the treatment portion 274 is selected in accordance with the shape of the STG tendon 312 of the implant tendon 310.

The anterior cruciate ligament 152 anatomically branches into two fiber bundles, so it is also preferable that two holes are made in each of the femur 112 and tibia 114, and that the implant tendon 310 is passed through the respective holes.

According to the first procedure example, it can be considered as follows.

Each of an area of the footprint region 162 of the femur 112 of the anterior cruciate ligament 152 and an area of the footprint region 172 of the tibia 114 is small. Under the arthroscope, the treatment portion 274 of the ultrasonic treatment instrument 252 can be pressed directly onto the footprint region 162 of the femur 112 to cut the femur 112 toward the outside, thus the bone hole 320 can be formed to securely fix the implanted tendon 310 to an anatomical position. The approximately rectangular bone hole 320 can be formed without needing to expand the bone hole with the dilator. At this time, a mechanically excessive force is not applied to the femur 112, so it is possible to perform a procedure of forming the bone hole 320 in a state where it is difficult for the femur 112 to be fractured.

The outer shape of the STG tendon 312 of the implant tendon 310 is different from a circular shape, and is a rectangular shape, an elliptical shape or the like. For example, when the STG tendon 312 with an outer shape of 5 mm×4 mm=20 mm$^2$ is to be inserted into a circular hole, a diameter of the circular hole needs to be about 6.5 mm. In a case where the circular hole is used in this way, about 40% of a region of the circular hole is a space other than a region in which the STG tendon 312 of the implant tendon 310 is disposed. The joint liquid permeates this space, and the STG tendon 312 of the implant tendon 310 may slowly form the ligament.

By suitably selecting the treatment portion 274 of the ultrasonic treatment instrument 252, the concave hole or the through hole having any shape such as the elliptical shape or the polygonal shape can be formed in a suitable depth. Therefore, when the concave holes 320 and 324 are suitably formed in accordance with the outer shape of the STG tendon 312 as shown in FIG. 22A to FIG. 22E, the space volume between the concave holes 320 and 324 and the STG tendon 312 can be smaller, and an amount of the femur 112 and the tibia 114 to be cut can be smaller. In the present embodiment, the ultrasonic probe 266 is suitably selected in accordance with the outer shape of the STG tendon 312, so that it is possible to suitably form the concave holes 320 and 324 while decreasing the amount of bone to be cut. Thus, the STG tendon 312 is fixed to the suitably formed concave holes 320 and 324, whereby the implanted tendon 310 can form the ligament sooner.

That is, the concave holes 320 and 324 can be formed by using the ultrasonic treatment instrument 252 including the treatment portion 274 having the pillar-shaped portion 286a of a rectangular, approximately rectangular, elliptical or approximately elliptical cross section. Therefore, it is possible to form the concave holes 320 and 324 having the same outer shape or approximately the same outer shape as the outer shape of the STG tendon 312 of the implant tendon 310, and it is possible to appropriately bury and fix the STG tendon 312 into the concave holes 320 and 324.

Also, in a case where the drilled hole 322 is formed with the drill 234 after the concave hole 320 is formed with the treatment portion 274 of the ultrasonic treatment instrument 252, it is possible to perform a treatment of forming the drilled hole 322 in a state where the distal end of the drill 234 is fitted into the bottom surface of the previously formed concave hole 320. As a result, in a case of using this procedure, it is easy to match the central axis of the previously formed concave hole 320 with the central axis of the drilled hole 322 to be formed later. Furthermore, when the ultrasonic treatment instrument 252 is used, it is easier to form the concave hole or the through hole at a desired position as compared with a case where the drill is used. Therefore, in the desired regions of the footprint regions 162 and 172 of the anterior cruciate ligament 152, it is possible to form the bone holes 320 and 324 in which the STG tendon 312 of the implant tendon 310 is disposed without projecting, to the greatest extent possible, in a desired orientation.

Because of this, in the femur 112, invasion into a peripheral tissue of the footprint regions 162 and 172 of the anterior cruciate ligament 152 is prevented.

As described above, the lateral cross section of the implant tendon 310 varies in vertical×horizontal lengths. In a case where the ultrasonic treatment instrument 252 shown in FIG. 16 is used, a cross section of each of the concave holes 320 and 324 is, for example, rectangular. For this reason, when the concave holes 320 and 324 are formed in the appropriate orientation, it is easy to optimize the orientation in a state where the STG tendon 312 of the implant tendon 310 is implanted.

In this procedure, the example has been described where the suitable regions of the footprint regions 162 and 172 are marked, but the marking is not necessarily required.

Next, as a second procedure example, two examples of a case where the implant tendon (the BTB tendon) 330 is used will briefly be described.

Here, the example is described where a patellar tendon 332 to which bone fragments 332a and 332b adhere at both ends is used as the implant tendon 330. One bone fragment 332a is a part of a patella (not shown). The bone fragment 332a on a patella side has an approximately triangular pillar shape. The other bone fragment 332b is a part of the tibia 114. The bone fragment 332b on a tibia 114 side is rectangular parallelepiped. An outer shape of each of the bone fragments 332a and 332b has a size of, for example, about 10 mm×5 mm. Such a tendon to be implanted is referred to as the BTB tendon.

Figure 23:
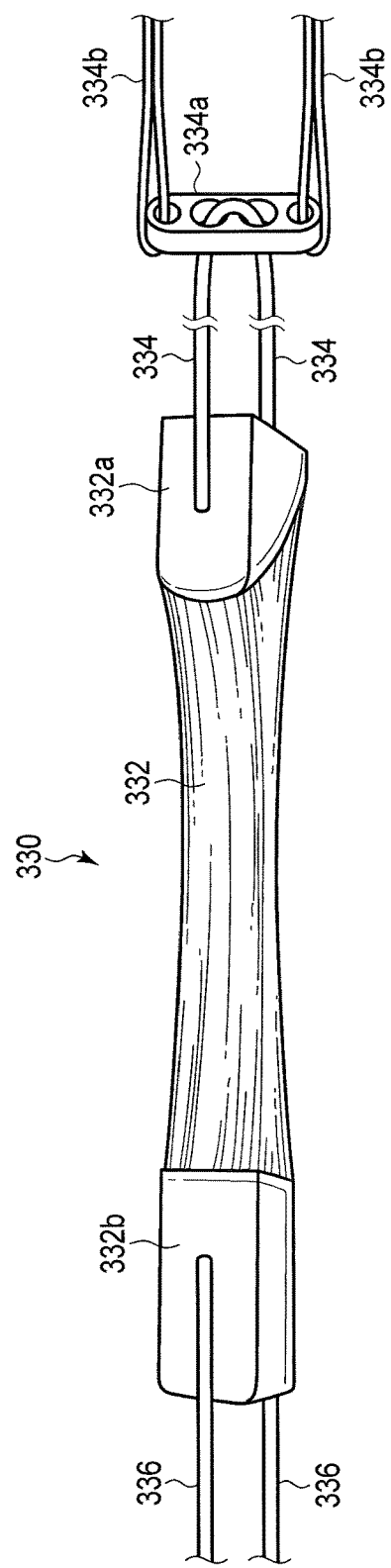
FIG. 23 is a schematic view of an implant tendon which includes a BTB tendon for use in the reconstruction of the anterior cruciate ligament.

As shown in FIG. 23, the implant tendon 330 has the BTB tendon 332, a suspension fixture 334a disposed in the bone fragment 332a at one end of the BTB tendon 332 via a suture thread 334 and, for example, a pair of suture threads 336 fixed to the bone fragment 332b at the other end of the BTB tendon 332. It is to be noted that a string 334b wound around the fixture 334a is used in taking the fixture 334a from the knee joint 100 to the outside of the femur 112 through later-described concave holes 340a and 340b and a later-described through hole 342.

It is preferable that the later-described bone holes 340a and 340b, into which the bone fragment 332a of the BTB tendon 332 is inserted, and later-described bone holes 344a and 344b, into which the bone fragment 332b is inserted, have sizes and shapes which conform to an outer shape of the BTB tendon 332, respectively.

It is preferable that the BTB tendon 332 is sampled before dissecting a region to which the damaged anterior cruciate ligament 152 adheres. Thus, a size of the outer shape of each of the bone fragments 332a and 332b is beforehand measured.

A first example where the BTB type of implant tendon 330 is used will be described with reference to FIG. 24A to FIG. 24G. FIG. 24A to FIG. 24G schematically show a state where the femur 112, the tibia 114, and the joint cavity 136 of the knee joint 100 are seen from the anterior side. Arrows in FIG. 24A to FIG. 24F indicate an excising direction of the bone.

Here, a procedure is performed using an inside out method. Descriptions of those parts that are the same as in the procedure of the STG tendon 312 are omitted whenever possible.

Figure 24A:
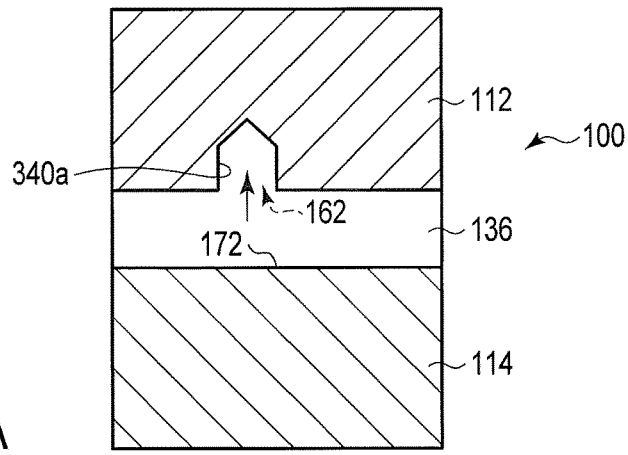
FIG. 24A is a schematic view showing a procedure of the reconstruction of the anterior cruciate ligament and showing a state where a concave hole is formed from the inside of the knee joint to the footprint region of the anterior cruciate ligament of the femur of the knee joint with the ultrasonic treatment instrument.

The first concave hole 340a shown in FIG. 24A is formed straight to the femur 112 in a region of the footprint region 162 of the femur 112 with the treatment portion 274 of the ultrasonic treatment instrument 252. The first concave hole 340a is formed similarly to the concave hole 300 shown in FIG. 18B.

Figure 24B:
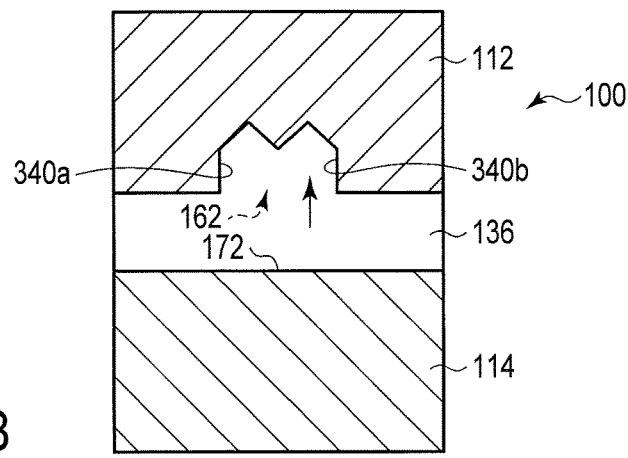
FIG. 24B is a schematic view showing a state where a concave hole is formed at a position adjacent to the concave hole of the femur in the state shown in FIG. 24A.

The second concave hole 340b shown in FIG. 24B is formed adjacent to the first concave hole 340a with the same treatment portion 274 of the ultrasonic treatment instrument 252. At this time, the treatment is performed while the treatment portion 274 of the ultrasonic treatment instrument 252 is left in the joint 100. The second concave hole 340b is formed similarly to the concave hole 300 shown in FIG. 18B. The first concave hole 340a must be in communication with the second concave hole 340b. Therefore, when necessary, a bone tissue between the first concave hole 340a and the second concave hole 340b is removed by cutting. In this way, a bone hole of an outer shape required for the concave holes 340a and 340b is formed into a desired size and a desired shape by pressing the treatment portion 274 of the ultrasonic treatment instrument 252 at a position adjacent to the bone hole 340a once or a number of times. Therefore, an outer shape of 4 mm×5 mm of one concave hole 340a is continuous with an outer shape of 4 mm×5 mm of another concave hole 340b, additionally, the treatment is suitably performed with the treatment portion 274 of the ultrasonic treatment instrument 252. Because of this, the concave holes 340a and 340b cooperate to form one bone hole of an outer shape of 10 mm×5 mm into which the bone fragment 332a is insertable.

Figure 24C:
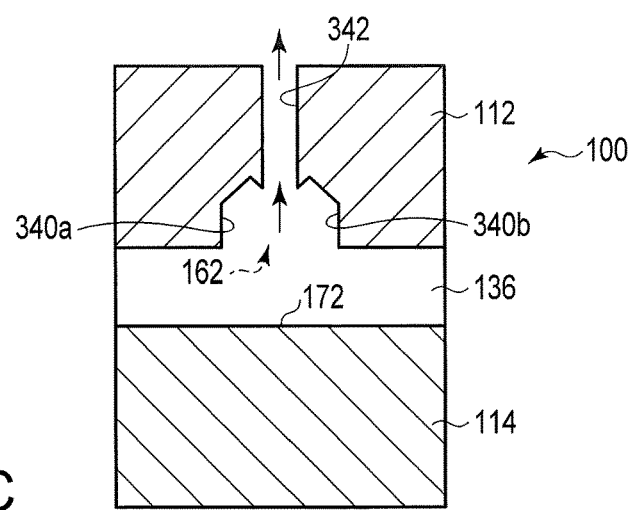
FIG. 24C is a schematic view showing a state where a through-hole is formed from the inside of the joint to the concave hole of the femur in the state shown in FIG. 24B.

Afterward, the through hole (a drilled hole) 342 shown in FIG. 24C is formed straight to the femur 112 through the region of the footprint region 162 of the femur 112 with the drill 234. That is, a hole is cut from the inside of the joint 100 toward the outside of the femur 112 to form the bone hole 342. To the femur 112, the drill (a first treatment unit) 234 is inserted from the suitable portal 104 into the joint cavity 136 of the knee joint 100. Furthermore, a diameter of the drill 234 is adjusted into such a diameter that the suspension fixture 334a can pass from the joint cavity 136 side through the cortical bone on the outer side of the femur. The drill 234 is pulled out from the portal 104 after the through hole 342 is formed.

Figure 24D:
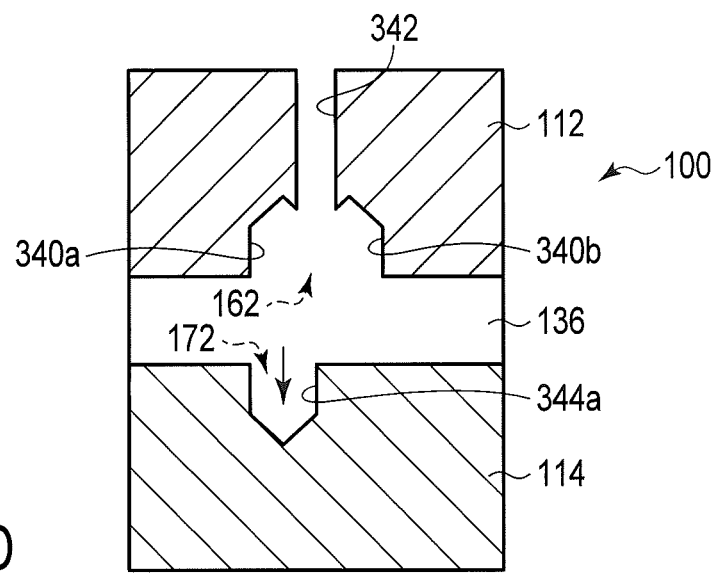
FIG. 24D is a schematic view showing a state where a concave hole is formed from the inside of the knee joint to the footprint region of the anterior cruciate ligament of the tibia of the knee joint in the state shown in FIG. 24C with the ultrasonic treatment instrument.

The concave hole 344a shown in FIG. 24D is formed in a region of the footprint region 172 of the tibia 114 by use of the ultrasonic treatment instrument 252. The concave hole 344a is formed similarly to the concave hole 300 shown in FIG. 18B.

Figure 24E:
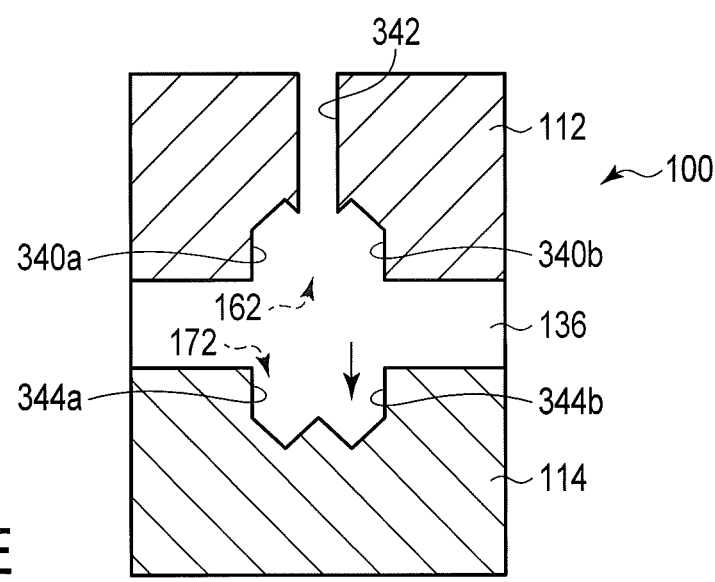
FIG. 24E is a schematic view showing a state where a concave hole is formed at a position adjacent to the concave hole of the tibia in the state shown in FIG. 24D.

The concave hole 344b that is continuous with the concave hole 344a as shown in FIG. 24E is formed in the region of the footprint region 172 of the tibia 114 by use of the ultrasonic treatment instrument 252. The concave hole 344b is formed similarly to the concave hole 300 shown in FIG. 18B. A bone hole of an outer shape required for the concave holes 344a and 344b is formed into a desired size and a desired shape by pressing the treatment portion 274 of the ultrasonic treatment instrument 252 at a position adjacent to the bone hole 344a once or a number of times. Therefore, an outer shape of 4 mm×5 mm of one concave hole 344a is continuous with an outer shape of 4 mm×5 mm of another concave hole 344b, and additionally, a treatment is suitably performed with the treatment portion 274 of the ultrasonic treatment instrument 252. Thus, the concave holes 344a and 344b cooperate to form one bone hole of an outer shape of 10 mm×5 mm into which the bone fragment 332b can be inserted.

Figure 24F:
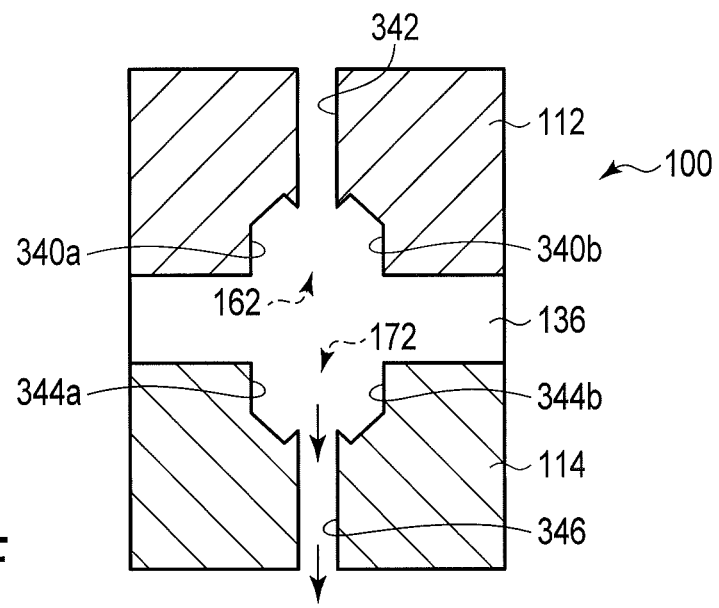
FIG. 24F is a schematic view showing a state where a through-hole is formed from the inside of the joint to the concave hole of the tibia in the state shown in FIG. 24E.
Figure 24G:
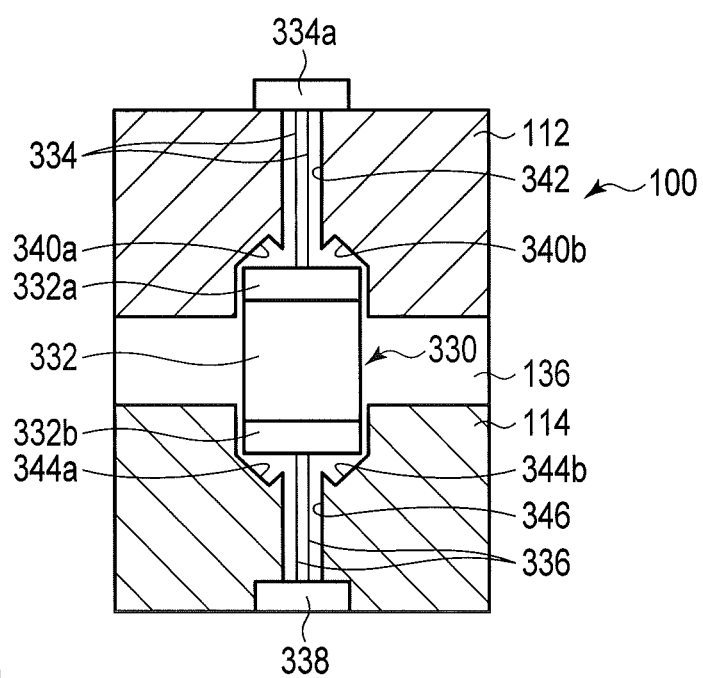
FIG. 24G is a schematic view showing a state where the implanted tendon including the BTB tendon shown in FIG. 23 is fixed to the femur and the tibia.

Subsequently, a through hole (a drilled hole) 346 shown in FIG. 24F is formed straight to the tibia 114 through the region of the footprint region 172 of the tibia 114 with the drill 234.

Further, for example, one bone fragment 332a of the implant tendon 330 by the BTB tendon 332 is inserted from the second portal 104 into the concave holes 340a and 340b of the femur 112. At this time, the fixture 334a is taken out from the femur 112 via the drilled hole 342. The one bone fragment 332a of the implant tendon 330 is disposed in accordance with an orientation of the concave holes 340a and 340b. An outer shape of the one bone fragment 332a of the implant tendon 330 is a triangular pillar shape as described above.

The other bone fragment 332b of the implant tendon 330 is disposed in the concave holes 344a and 344b of the tibia 114 to take the suture threads 336 attached to the bone fragment 332b to the outside of the tibia 114 via the drilled hole 346. Further, a tensile force of the implanted tendon 330 is suitably adjusted in accordance with the bent state of the knee joint 100 to fix the suture threads 336 of the implanted tendon 330 to an outer side of the tibia 114 with a fixture 338 such as a staple (a screw may be used) (see FIG. 24G).

A second example where the BTB type of implant tendon 330 is used will be described with reference to FIG. 25A to FIG. 25C. FIG. 25A to FIG. 25C schematically show a state where the femur 112, the tibia 114 and the joint cavity 136 of the knee joint 100 are seen from the anterior side. Arrows in FIG. 25A and FIG. 25B indicate an excising direction of the bone.

Two concave holes 350a and 350b shown in FIG. 25A are formed in the footprint region 162 of the femur 112 with the treatment portion 274 of the ultrasonic treatment instrument 252. At this time, each of the two concave holes 350a and 350b is formed similarly to the concave hole 300 of FIG. 18B. The concave holes 350a and 350b are adjacent to each other and communicate with each other.

Two concave holes 352a and 352b shown in FIG. 25B are formed in the footprint region 172 of the tibia 114 with the treatment portion 274 of the ultrasonic treatment instrument 252. At this time, each of the two concave holes 352a and 352b is formed similarly to the concave hole 300 of FIG. 18B. The two concave holes 352a and 352b are adjacent to each other and communicate with each other.

For example, one bone fragment 332a of the implant tendon 330 by the BTB tendon 332 is inserted from the second portal 104 into the concave holes 350a and 350b of the femur 112. The other bone fragment 332b is inserted into the concave holes 352a and 352b of the tibia 114. Furthermore, the one bone fragment 332a is fixed to the concave holes 350a and 350b of the femur 112 with a screw 338a. The other bone fragment 332b is fixed to the concave holes 352a and 352b of the tibia 114 with a screw 338b (see FIG. 25C).

At this time, the screws 338a and 338b can be disposed through the joint cavity 136. Therefore, it is not necessary to form through holes to the femur 112 and the tibia 114 by use of, for example, a drill or the like.

According to the second procedure example, it can be stated as follows.

The outer shape of each of the bone fragments 332a and 332b at the ends of the BTB tendon 332 of the implant tendon 330 is different from a circular shape and is a rectangular parallelepiped shape or an approximately triangular pillar shape. For example, when the BTB tendon 332 of 5 mm×10 mm=50 mm² is to be inserted into the circular hole, a diameter of the circular hole needs to be about 11 mm. In this case, a cross-sectional area of the circular hole is about 95 mm² and about a half becomes a space. The joint liquid permeates this space and formation of a ligament by the BTB tendon 332 of the implant tendon 330 might become slow.

Therefore, when the concave holes 340a, 340b, 344a and 344b are suitably formed in accordance with the outer shape of the bone fragments 332a and 332b of the BTB tendon 332 as shown in FIG. 24A to FIG. 24G, it is possible to decrease each of a space volume between the concave holes 340a and 340b and the bone fragment 332a of the BTB tendon 332, and a space volume between the concave holes 344a and 344b and the bone fragment 332b of the BTB tendon 332, and it is possible to decrease an amount of the femur 112 and the tibia 114 that is cut. In the present embodiment, the ultrasonic probe 266 is suitably selected in accordance with the outer shape of the bone fragments 332a and 332b of the BTB tendon 332, so that it is possible to suitably form the concave holes 340a, 340b, 344a, and 344b while decreasing the amount of cut bone. Further, the bone fragments 332a and 332b are fixed to the suitably formed concave holes 340a, 340b, 344a, and 344b, whereby it is possible to more quickly form the ligament by the implanted tendon 330.

That is, it is possible to form the concave holes 340a, 340b, 344a, and 344b by use of the ultrasonic treatment instrument 252 including the treatment portion 274 having the pillar-shaped portion 286a of the rectangular, approximately rectangular, elliptical, or approximately elliptical cross section. Because of this, it is possible to form the concave holes 340a, 340b, 344a, and 344b having the same outer shape or about the same outer shape as the outer shape of the bone fragments 332a and 332b of the BTB tendon 332 of the implanted tendon 330, and it is possible to appropriately bury and fix the bone fragments 332a and 332b into the concave holes 340a, 340b, 344a and 344b.

Furthermore, when the ultrasonic treatment instrument 252 is used, it is easier to form a position to form the concave hole or the through hole at a desired position as compared with a case where the drill is used. For this reason, it is possible to form the bone holes 340a, 340b, 344a, and 344b in which the end portions of the implanted tendon 330 are disposed to not project to the greatest extent possible, to the footprint regions 162 and 172 of the anterior cruciate ligament 152. Therefore, in the femur 112, invasion into a peripheral tissue of the footprint region 162 of the anterior cruciate ligament 152 is prevented.

Also, as described above, the lateral cross section of the implant tendon 330 varies in vertical×horizontal lengths. In a case where the ultrasonic treatment instrument 252 shown in FIG. 16 is used, the cross section of each concave hole is, for example, rectangular. Therefore, when the concave holes are formed in the appropriate orientation, it is easy to optimize the orientation in a state where the BTB tendon 332 of the implant tendon 330 is implanted.

Figure 22E:
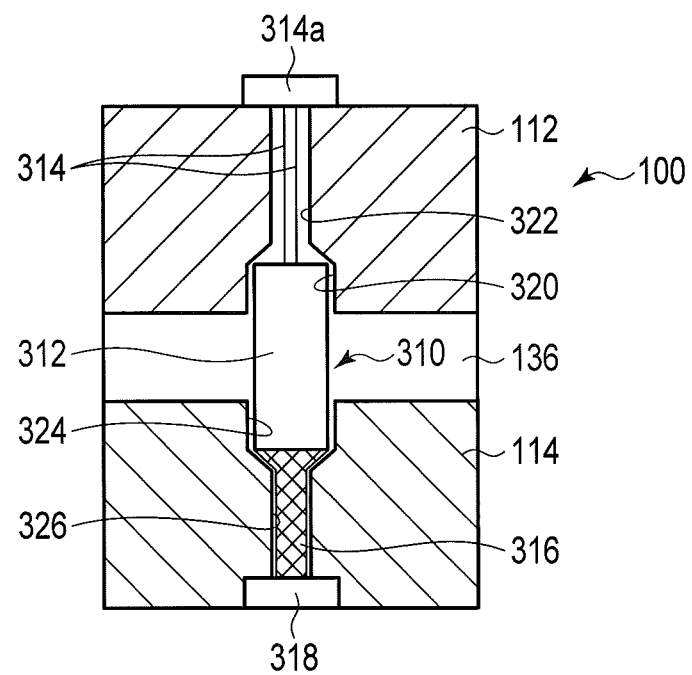
FIG. 22E is a schematic view showing a state where the implanted tendon including the STG tendon shown in FIG. 21 is fixed to the femur and the tibia.
Figure 26:
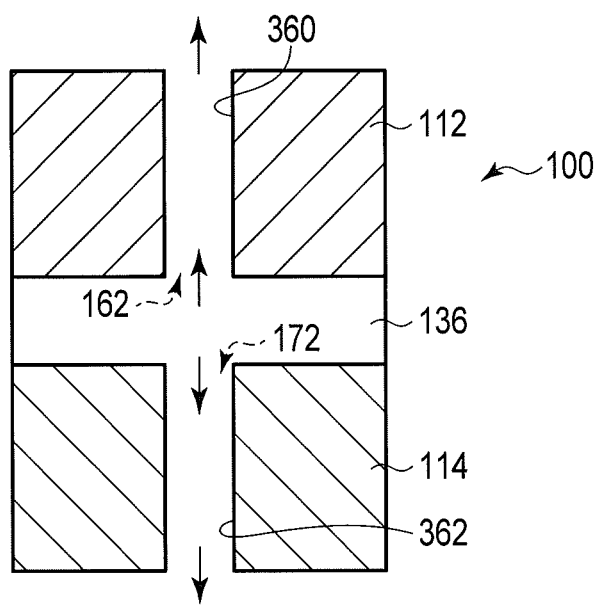
FIG. 26 is a schematic view showing a state where in the reconstruction of the anterior cruciate ligament, a through hole is formed from the inside of the knee joint to the footprint region of the anterior cruciate ligament of the femur of the knee joint with the ultrasonic treatment instrument, and a through-hole is formed from the inside of the joint to the footprint region of the anterior cruciate ligament of the tibia with the ultrasonic treatment instrument.

In the above-mentioned procedure, the example has been described where the concave hole 300 shown in FIG. 18B is formed in the treatment using the ultrasonic treatment instrument 252. In the ultrasonic treatment instrument 252 of the treatment system 10, energy can be suitably adjusted, and the probe 266 having the suitable treatment portion 274 shown in FIG. 19A to FIG. 20B can suitably be selected. In this case, not only the concave holes, but also a through hole 360 shown in FIG. 26 can be formed. FIG. 26 shows a state where, for example, by the inside out method, the through hole 360 is formed from the footprint region 162 of the femur 112 to the outside of the femur 112, and a through hole 362 is formed from the footprint region 172 of the tibia 114 to the outside of the tibia 114. That is, it is possible to form the through hole 360 as a through hole extending through the knee joint 100 and the outside of the femur 112 in the state where the ultrasonic vibration is transmitted to the treatment portion 274 of the ultrasonic treatment instrument 252. In this case, in the bone holes 360 and 362, for example, the implant tendon 310 including the STG tendon 312 is disposed and fixed in the same manner as shown in FIG. 22E.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical procedure of fixing an implanted tendon to a first bone and a second bone of a joint when performing ligament reconstruction using an ultrasonic treatment instrument, the implanted tendon having a longitudinal axis and first and second ends, each of the first and second ends having non-circular cross sections perpendicular to the longitudinal axis of the implanted tendon, the surgical procedure comprising:
    inserting a treatment portion of the ultrasonic treatment instrument into the joint;
    bringing the treatment portion of the ultrasonic treatment instrument into contact with a first region of the first bone of the joint to which a ligament was once attached or currently adheres;
    applying ultrasonic vibration through the treatment portion to the first region, thereby forming a first concave hole in the first bone with a closed bottom surface in the first region, wherein the first concave hole is non-circular in cross section;
    bringing the treatment portion of the ultrasonic treatment instrument into contact with a second region of the second bone of the joint to which the ligament was once attached or currently adheres;
    applying ultrasonic vibration through the treatment portion to the second region, thereby forming a second concave hole in the second bone with a closed bottom surface in the second region, wherein the second concave hole is non-circular in cross section;
    inserting and fixing the first end of the implanted tendon into the first concave hole; and
    inserting and fixing the second end of the implanted tendon into the second concave hole.

2. The procedure according to claim 1, wherein the cross section of the first concave hole is a polygonal shape, an approximately polygonal shape, an elliptical shape, or an approximately elliptical shape.

3. The procedure according to claim 1, wherein the forming the first concave hole includes forming the first concave hole into a shape suitable to receive the implanted tendon.

4. The procedure according to claim 1, wherein the treatment portion has a non-circular periphery having a polygonal shape, an approximately polygonal shape, an elliptical shape, or an approximately elliptical shape.

5. The procedure according to claim 1, wherein a cross section of the implanted tendon, which is perpendicular to the longitudinal axis of the implanted tendon, is an approximately polygonal shape or an approximately elliptical shape.

6. The procedure according to claim 1, comprising pressing the treatment portion against the first bone along a longitudinal axis of the treatment instrument while inputting the ultrasonic vibration to the treatment portion.

7. The procedure according to claim 1, comprising determining an orientation of the treatment portion of the ultrasonic treatment instrument with respect to the first bone.

8. The procedure according to claim 1, comprising determining an orientation of the treatment portion with respect to the first bone and an orientation of the first concave hole with respect to the first bone so as to optimize an orientation of the implanted tendon.

9. The procedure according to claim 1, wherein:
    the joint is a knee joint;
    the first one is a femur; and
    the second bone is a tibia.

10. The procedure according to claim 1,
    wherein the first concave hole and second concave hole are formed to optimize an orientation of the implanted tendon.

11. The surgical procedure according to claim 1, further comprising measuring a size of an outer shape of each of the first and second ends of the implanted tendon,
    wherein the first concave hole is formed in accordance with the outer shape of the first end of the implanted tendon and the second concave hole is formed in accordance with the outer shape of the second end of the implanted tendon.

12. The surgical procedure according to claim 11, wherein
    the outer shape of the first concave hole conforms to or approximately conforms to the outer shape of the first end of the implanted tendon, and
    the outer shape of the second concave hole conforms to or approximately conforms to the outer shape of the second end of the implanted tendon.

13. A surgical procedure of fixing an implanted tendon to a first bone and a second bone of a joint when performing ligament reconstruction using an ultrasonic treatment instrument, the surgical procedure comprising:
    inserting a treatment portion of the ultrasonic treatment instrument into the joint;
    bringing the treatment portion of the ultrasonic treatment instrument into contact with a first region of the first bone of the joint to which a ligament was once attached or currently adheres;
    applying ultrasonic vibration through the treatment portion to the first region, thereby forming a first concave hole in the first bone with a closed bottom surface in the first region;
    brining the treatment portion of the ultrasonic treatment instrument into contact with a second region of the second bone of the joint to which the ligament was once attached or currently adheres;
    applying ultrasonic vibration through the treatment portion to the second region thereby forming a second concave hole in the second bone with a closed bottom surface in the second region;
    inserting and fixing one end of the implanted tendon into the first concave hole;
    inserting and fixing another end end of the implanted tendon into the second concave hole, and
    forming, by the treatment portion at a position adjacent to the first concave hole, a third concave hole in the first bone that is continuous with the first concave hole, the first concave hole and the third concave hole having parallel axes.

14. The procedure according to claim 13, wherein:
    the first concave hole and the third concave hole form a concave unified hole in the first bone, and
    an outer shape of the unified hole has a polygonal shape, an approximately polygonal shape, an elliptical shape, or an approximately elliptical shape.

* * * * *